US012370240B2

(12) United States Patent
Chalberg et al.

(10) Patent No.: US 12,370,240 B2
(45) Date of Patent: Jul. 29, 2025

(54) METHODS AND COMPOSITIONS FOR TREATING OSTEOARTHRITIS

(71) Applicants: Genascence Corporation, Palo Alto, CA (US); Mayo Foundation for Medical Education and Research, Rochester, MN (US)

(72) Inventors: Thomas W. Chalberg, Palo Alto, CA (US); Christopher Howard Evans, Cohasset, MA (US)

(73) Assignees: Genascence Corporation, Palo Alto, CA (US); Mayo Foundation for Medical Education and Research, Rochester, MN (US)

( * ) Notice: Subject to any disclaimer, the term of this patent is extended or adjusted under 35 U.S.C. 154(b) by 949 days.

(21) Appl. No.: 17/295,588

(22) PCT Filed: Nov. 26, 2019

(86) PCT No.: PCT/US2019/063370
§ 371 (c)(1),
(2) Date: May 20, 2021

(87) PCT Pub. No.: WO2020/112853
PCT Pub. Date: Jun. 4, 2020

(65) Prior Publication Data

US 2022/0016213 A1 Jan. 20, 2022

Related U.S. Application Data

(60) Provisional application No. 62/772,333, filed on Nov. 28, 2018.

(51) Int. Cl.

| | |
|---|---|
| ***A61K 48/00*** | (2006.01) |
| ***A61K 38/20*** | (2006.01) |
| ***A61P 19/02*** | (2006.01) |
| ***C12N 15/86*** | (2006.01) |

(52) U.S. Cl.
CPC ...... *A61K 38/2006* (2013.01); *A61K 48/0066* (2013.01); *A61K 48/0075* (2013.01); *A61P 19/02* (2018.01); *C12N 15/86* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,228,356 | B1 | 5/2001 | Glorioso et al. |
| 2003/0235589 | A1 * | 12/2003 | Demopulos et al. |
| 2008/0187576 | A1 | 8/2008 | Ghivizzani et al. |
| 2012/0065094 | A1 | 3/2012 | Attur et al. |
| 2016/0030512 | A1 * | 2/2016 | Wehling et al. |
| 2018/0223362 | A1 | 8/2018 | Kornman et al. |

FOREIGN PATENT DOCUMENTS

| | | | |
|---|---|---|---|
| CA | 3046347 | A1 | 6/2018 |
| WO | WO9728828 | A1 | 8/1997 |
| WO | WO9732597 | A1 | 9/1997 |
| WO | WO0111034 | A2 | 2/2001 |
| WO | WO0125435 | A2 | 4/2001 |
| WO | WO0192551 | A2 | 12/2001 |
| WO | WO2006066066 | A2 | 6/2006 |
| WO | WO2007124148 | A2 | 11/2007 |
| WO | WO2009135219 | A2 | 11/2009 |
| WO | WO2015052154 | A1 | 4/2015 |
| WO | WO 2017/147649 | A1 * | 9/2017 |
| WO | WO2018035441 | A1 | 2/2018 |
| WO | WO2018035451 | A1 | 2/2018 |
| WO | WO2018106956 | A2 | 6/2018 |

OTHER PUBLICATIONS

Bartlett, JS, Feb. 22, 2018 (Geneseq Accession No. BFC59772, computer printout, pp. 1-2) (Bartlett SEQ ID No. 4).*
Attur et al., Radiographic severity of knee osteoarthritis is conditional on interleukin 1 receptor antagonist gene variations, Ann Rheum Dis, 2010; 69:856-861.
Attur et al., Increased IL-1 beta gene expression in peripheral blood leukocytes is associated with increased pain and predicts risk for progression of symptomatic knee osteoarthritis, Arthritis Rheum, Jul. 2011; 63(7):1908-1917.
Attur et al., Plasma levels of interleukin-1 receptor antagonist (IL1Ra) predict radiographic progression of symptomatic knee osteoarthritis (SKOA), Osteoarthritis Cartilage, Nov. 2015, 23(11):1915-1924.
Attur et al., Interleukin 1 receptor antagonist (IL1RN) gene variants predict radiographic severity of knee osteoarthritis and risk of incident disease, Ann Rheum Dis, 2020; 79:400-407.
Braun et al., Diagnosis of Osteoarthritis: Imaging, Bone, Aug. 2012; 51(2):278-288.
Evans et al., Getting arthritis gene therapy into the clinic, Nat Rev Rheumatol, Apr. 2011; 7(4):244-249.
Evans et al., Arthritis Gene Therapy: A Brief History and Perspective, Chapter 6, Translating Gene Therapy to the Clinic, 2015, pp. 85-98.
Evans, Safety of Intra-Articular Sc-rAAV2.5IL-1Ra in Subjects With Moderate Knee OA (AAVIL-1Ra), ClinicalTrials.gov Identifier: NCT02790723, First Posted Jun. 6, 2016, 7 pages.
Evans et al, Gene Delivery to Joints by Intra-Articular Injection, Human Gene Therapy, 2017, vol. 29, No. 1, 13 pages.
Evans, Arthritis Gene Therapy Using Interleukin-1 Receptor Antagonist, Arthritis & Rheumatology, vol. 70, No. 11, Nov. 2018, pp. 1699-1701.
Evans et al., Arthritis gene therapy is becoming a reality, Nat Rev Rheumatol, Jul. 2018; 14(7):381-382.

(Continued)

*Primary Examiner* — Michael D Burkhart
(74) *Attorney, Agent, or Firm* — Melissa L. Nakamoto; Bret E. Field; Bozicevic, Field & Francis LLP

(57) ABSTRACT

Methods for treating a human suffering from osteoarthritis are provided. Aspects of the methods include intra-articularly administering to the human a dosage comprising a nucleic acid coding sequence for a human interleukin-1 receptor antagonist (IL-1Ra) to treat the human suffering from osteoarthritis. Also provided are compositions for use in practicing the methods.

20 Claims, No Drawings

Specification includes a Sequence Listing.

(56) References Cited

OTHER PUBLICATIONS

Kerkhof et al., Large-scale meta-analysis of interleukin-1 beta and interleukin-1 receptor antagonist polymorphisms on risk of radiographic hip and knee osteoarthritis and severity of knee osteoarthritis, Osteoarthritis and Cartilage 19 (2011) 265-271.
Wu et al., IL-1 receptor antagonist gene as a predictive biomarker of progression of knee osteoarthritis in a population cohort, Osteoarthritis Cartilage, Jul. 2013; 21(7):930-938.
Levings et al., Gene Therapy for Osteoarthritis: Pharmacokinetics of Intra-Articular Self-Complementary Adeno-Associated Virus Interleukin-1 Receptor Antagonist Delivery in an Equine Model, Hum Gene Ther Clin Dev, Jun. 2018; 29(2):90-100.
Levings et al., scAAV-Mediated IL-1Ra gene delivery for the Treatment of Osteoarthritis: Test of Efficacy in an Equine Model, Human Gene Therapy, 2017, 36 pages.
Levings et al., Self-Complementary Adeno-Associated Virus-Mediated Interleukin-1 Receptor Antagonist Gene Delivery for the Treatment of Osteoarthritis: Test of Efficacy in an Equine Model, Hum Gene Ther Clin Dev, Jun. 2018; 29(2):101-112.
Mease et al., Local delivery of a recombinant adenoassociated vector containing a tumour necrosis factor a antagonist gene in inflammatory arthritis: a phase 1 dose-escalation safety and tolerability study, Ann Rheum Dis 2009;68:1247-1254.
Mease et al., Safety, tolerability, and clinical outcomes after intraarticular injection of a recombinant adeno-associated vector containing a tumor necrosis factor antagonist gene: results of a phase 1/2 Study, J Rheumatol, Apr. 2010; 37(4):692-703.
Wang et al., Safety and biodistribution assessment of sc-rAAV2. 5IL-1Ra administered via intra-articular injection in a mono-iodoacetateinduced osteoarthritis rat model, Molecular Therapy—Methods & Clinical Development (2015) 1, 15052, 10 pages.
Wang et al., Safety and biodistribution assessment of sc-rAAV2. 5IL-1Ra administered via intra-articular injection in a mono-iodoacetateinduced osteoarthritis rat model, Molecular Therapy—Methods & Clinical Development (2016) 3, 15052.

* cited by examiner

METHODS AND COMPOSITIONS FOR TREATING OSTEOARTHRITIS

CROSS-REFERENCE TO RELATED APPLICATION

This application is a U.S. National Stage Application of PCT Application No. PCT/US2019/063370 filed Nov. 26, 2019, which application, pursuant to 35 U.S.C. § 119 (e), claims priority to the filing date of U.S. Provisional Patent Application Ser. No. 62/772,333 filed Nov. 28, 2018; the disclosures of which applications are herein incorporated by reference.

GOVERNMENT RIGHTS

This invention was made with government support under NS066865 awarded by the National Institutes of Health and supported under W81XWH-16-1-0540 awarded by the U.S. Army. The government has certain rights in the invention.

REFERENCE TO AN ELECTRONIC SEQUENCE LISTING

The contents of the electronic sequence listing (GENAS-001WO_Seq_Listing_ST25.txt; Size: 29,178 bytes; and Date of Creation: Jan. 7, 2020) is herein incorporated by reference In its entirety.

INTRODUCTION

Osteoarthritis (OA) affects over 27 million Americans and is the leading cause of disability among the elderly (Lawrence, et al., "Estimates of the prevalence of arthritis and other rheumatic conditions in the United States. Part II." Arthritis and rheumatism (2008) 58(1):26-35). Patients with OA are also at higher risk of death (Nuesch et al., "All cause and disease specific mortality in patients with knee or hip osteoarthritis: population based cohort study," Bmj (2011) 342:d1165). The cost of OA to our health care system is estimated to be over $100 billion per annum (Kotlarz et al., "Insurer and out-of-pocket costs of osteoarthritis in the US: evidence from national survey data," Arthritis and rheumatism (2009) 60(12):3546-3553). Such statistics reflect the fact that OA is both incurable and remarkably resistant to treatment. Moreover, the incidence and prevalence of OA will rise with demographic changes in western societies. Several circumstances combine to bring this about.

Most fundamentally, the etiopathophysiology of OA is poorly understood. To some degree this is a hangover from an earlier mindset in which OA was considered an ineluctable result of wear and tear, and therefore resistant to pharmacological intervention. Studies into the biology of the disease process were therefore delayed and only recently have solid therapeutic targets emerged.

The earliest and predominant symptom of OA is pain (McCarberg & Tenzer, "Complexities in the pharmacologic management of osteoarthritis pain," Current medical research and opinion (2013) 29(5):539-548). Pain normally arises late in the disease process, by which time there is often considerable structural alteration in the affected joint, including loss of articular cartilage, sclerosis of the subchondral bone, the formation of osteophytes, and synovial inflammation (Loeser et al., "Osteoarthritis: a disease of the joint as an organ," Arthritis and rheumatism (2012) 64(6): 1697-1707). In knee joints, there is also meniscal damage. In the absence of any available disease-modifying osteoarthritis drugs (DMOADs) (Roubille et al., "New and emerging treatments for osteoarthritis management: will the dream come true with personalized medicine?," Expert opinion on pharmacotherapy (2013) 14(15):2059-2077) that halt or reverse disease progression, treatments are palliative. Because there is no effective way to intervene in the disease process, many patients progress to the point of needing total joint replacement surgery (Richmond, "Surgery for osteoarthritis of the knee," Rheumatic diseases clinics of North America (2013) 39(1):203-211). While a successful procedure, this involves major, expensive surgery with extensive rehabilitation. In many cases, there is a need for revision surgery to replace a prosthetic joint that has become dysfunctional.

There are currently no approved DMOADs, and the present standard of care is palliative. As reflected in the most recent guidelines for treating OA of the knee issued by the American College of Rheumatology (ACR) in 2012 (Hochberg et al., "American College of Rheumatology 2012 recommendations for the use of nonpharmacologic and pharmacologic therapies in osteoarthritis of the hand, hip, and knee," Arthritis care & research (2012) 64(4):465-474) and the American Academy of Orthopaedic Surgeons (AAOS) in 2013 (Jevsevar et al., "The American Academy of Orthopaedic Surgeons evidence-based guideline on: treatment of osteoarthritis of the knee, 2nd edition," The Journal of bone and joint surgery American (2013) 95(20):1885-1886), present approaches to treatment fall into three progressive categories.

Non-pharmacological therapy includes a range of strategies such as patient education and self-help, exercise programs and weight loss. Pharmacological therapy includes the use of acetaminophen, non-steroidal anti-inflammatory drugs (NSAIDs), opiates and the intra-articular injection of glucocorticoids or hyaluronic acid. NSAIDs bring partial relief to many patients but are associated with upper GI bleeding and kidney failure, of special concern in the present context as many individuals with OA are elderly. The intra-articular injection of glucocorticoids brings rapid relief in many cases, but the effects usually persist for only a few weeks. Repeated injection of glucocorticoids is impractical and counter-indicated because of concerns about infection and evidence that sustained, high doses of glucocorticoids damage articular cartilage. The benefits of the intra-articular injection of hyaluronic acid (viscosupplementation) are disputed; the ACR makes no recommendation on this score, while the AAOS no longer recommends it. The intra-articular injection of mesenchymal stem cells (MSCs) and autologous blood products, such as platelet-rich plasma, is increasingly popular but lacking the highest clinical evidence of safety and efficacy and not approved by the FDA for OA.

The latest recommendations from the Osteoarthritis Research Society International and European League Against Rheumatism for treatment of OA of the knee do not differ greatly from those of the ACR and AAOS.

The recommendations of the various bodies highlight the paucity of treatment options for OA and the complete lack of reliably effective pharmacologic interventions. Even when there is some response to therapy, it addresses only the signs and symptoms, not disease progression. When treatment fails to control the symptoms and progression of OA, surgical intervention may be indicated.

Arthroscopic lavage and debridement have been widely used to provide symptomatic relief, but this approach has declined following evidence that its effects are no greater than placebo. An osteotomy is sometimes performed to realign the forces in the knee joint, so that load is now born by areas of intact cartilage. This measure can provide relief for several years until the newly weight-bearing articular cartilage erodes and symptoms reappear. In general, osteotomy is viewed as a delaying tactic that buys time until the surgical implantation of a prosthetic knee joint. Many patients progress to the point of needing total joint replacement, and over 700,000 artificial knees were surgically implanted last in year in the US (Center for Disease Control: FastStats. http://wwwcdcgov/nchs/fastats/inpatient-surgeryhtm 2015). The latter statistic demonstrates very clearly the prevalence of knee OA and how little we can do about its progression.

Accordingly, one of the most common, expensive and debilitating diseases in the western world is incurable, very difficult to treat and has few therapeutic options. These circumstances reflect the urgency for alternative, new, effective treatments.

SUMMARY

Methods for treating a human suffering from osteoarthritis are provided. Aspects of the methods include intra-articularly administering to the human a dosage comprising a nucleic acid coding sequence for a human interleukin-1 receptor antagonist (IL-1Ra) to treat the human suffering from osteoarthritis. Also provided are compositions for use in practicing the methods.

DETAILED DESCRIPTION

Methods for treating a human suffering from osteoarthritis are provided. Aspects of the methods include intra-articularly administering to the human a dosage comprising a nucleic acid coding sequence for a human interleukin-1 receptor antagonist (IL-1Ra) to treat the human suffering from osteoarthritis. Also provided are compositions for use in practicing the methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

As summarized above, the present disclosure provides methods and compositions for treating a human suffering from osteoarthritis. The term "osteoarthritis" is used in its conventional sense to refer to type of arthritis caused by breakdown and eventual loss of cartilage in the joints. Osteoarthritis (OA) is also known as degenerative arthritis and degenerative joint disease. Clinically, OA is characterized by articular cartilage degradation followed by joint space narrowing. Multiple causative factors have been implicated, including: joint trauma, congenital dysplasia and aging. OA is also thought of as a disease that can occur insidiously during aging. Regardless of the underlying cause, the clinical findings in patients with OA are almost universal. Patients typically complain of pain, stiffness, decreased range of motion, palpable grinding within the joint (crepitus), swelling and eventual joint enlargement or deformity. Macroscopically, the articular cartilage surface develops areas of focal damage and softening early in the disease process. As OA progresses, surface cartilaginous fibrillations and vertical clefts develop, and eventually there are large areas of full thickness cartilage loss with exposed, eburnated subchondral bone. Radiographically, this process is seen as progressive joint space narrowing (secondary to loss of the radiolucent articular cartilage), subchondral bony sclerosis and cyst formation, and the development of marginal osteophytes. Eventually, the cumulative effect of all of these changes leads to decreased use of the joint, muscular atrophy, and debilitating pain (Felson et al., (2000) Ann. Intern. Med., 133(8):635-646). Microscopically, the synovial and cartilaginous tissues undergo characteristic changes as OA progresses. These articular tissues show significantly increased cellular proliferation. Either before or concomitant with the development of surface fibrillations, the macromolecular framework of the matrix is disrupted, and the water content increases. This is accompanied by a decrease in the aggregation of proteoglycans, the concentration of aggrecans, and the length of the glycosaminoglycan chains. These changes lead to an increase in the overall permeability of the matrix which decreases the cartilage stiffness and makes it more susceptible to further biochemical and biomechanical damage.

At the molecular level, cartilage matrix degradation is orchestrated by immune and inflammatory signals. Multiple molecular players, including inflammatory cytokines such as IL-1 and TNF, and, matrix metalloproteinases, such as MMP-2, 9 and 13 and aggrecanases: ADAMTS4 and 5 have been implicated in this degradative process. Cascades of inflammatory cytokines and catabolic enzymes are released from the cells in the synovium to orchestrate cartilage degradation. Regardless of the initiating etiological factors, the events producing the pathological changes involve a cascade of biological processes (Malemud et al., (2003) Cells Tissues Organs, 174:34-48).

The OA that is treated by the methods described herein may vary. While the OA may be associated with any joint, in some instances the joint is OA of the hand, knee, hip, shoulder, ankle, elbow, temporomandibular joint, and spine, and combinations thereof. In some instances, the OA that is treated by methods as described herein is OA of the knee. In some instances, the OA that is treated by methods as described herein is OA of the spine. Where the OA is OA of the spine, the target spine joint may vary. In some instances, the target spine joint is a facet joint. In some instances, the target spine joint is an intravertebral disc joint.

By "treatment" it is meant that at least an amelioration of one or more symptoms, e.g., pain, associated with OA is achieved, where amelioration is used in a broad sense to refer to at least a reduction in the magnitude of a parameter, e.g., a symptom associated with the OA. As such, treatment also includes situations where a pathological condition, or at least symptoms associated therewith, are completely inhibited, e.g., prevented from happening, or stopped, e.g., terminated, such that the human no longer suffers from OA, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of OA in a human, and includes: (a) preventing the OA from occurring in a human which may be predisposed to the disease but has not yet been diagnosed as having it; (b) inhibiting the OA, i.e., arresting its development; or (c) relieving the OA, i.e., causing regression of the OA. Treatment may result in a variety of different physical manifestations, e.g., reduction in perceived pain, modulation of joint structure, etc. Treatment of ongoing OA, where the treatment stabilizes or reduces the undesirable clinical symptoms of the patient, occurs in some embodiments. Such treatment may be performed prior to complete loss of function in the affected tissues. The subject therapy may be administered prior to the symptomatic state of the disease, during the symptomatic stage of the disease, and in some cases after the symptomatic stage of the disease.

Embodiments of the methods include intra-articularly administering a dosage to the human, where the dosage includes a nucleic acid coding sequence for a human IL-1Ra so as to treat the human suffering from OA. As the dosage is intra-articularly administered, administration of the dosage results in the dosage being situated within a joint, e.g., at a synovial location, such as where the dosage is administered by entering a joint. The dosage may be intra-articularly administered using any convenient protocol, e.g., via delivery through a needle where the distal end has been positioned at the within the target joint, e.g., where the distal end of the needle is positioned at a synovial location such that delivery of the dosage out the distal end of the needle results in delivery of the dosage to the target joint. In some embodiments, the injection can be given under ultrasound guidance. In some cases, the ultrasound guidance can be used to confirm placement of the needle in the target joint. Alternatively, a needleless injection protocol may be employed, e.g., where the target joint does not include a fluid space suitable for needle delivery, e.g., where the target join is that of an intravertebral disc. As reviewed above, in some instances the target joint is a joint of the hand, knee, hip, shoulder, ankle, elbow, temporomandibular joint, or spine, and in some instances is a knee joint or spine joint.

Where desired, lavage (i.e., thorough rinsing out) of the joint may be performed prior to intra-articular administration of the dosage. Where lavage is performed, the irrigation or lavage of the joint and subsequent aspiration or removal of fluid, removes particulate matter and loose bodies floating in the joint. Such a lavage procedure may have beneficial effects with regard to pain relief. In some cases, the flushing of diseased synovial fluid containing irritants, a byproduct of OA, is also therapeutic. In some cases, a lavage procedure can be used to clear the joint of neutralizing antibodies to a gene therapy vector prior to administration. By way of non-limiting example, a patient is optionally assessed for the presence of neutralizing antibodies in the blood and/or synovial fluid of the target joint. If neutralizing antibodies are detected above a certain threshold, for example 1:5, 1:10, 1:20, 1:40, 1:60, 1:80, 1:100, 1:120, 1:160, 1:240, or 1:320, a lavage is performed prior to intra-articular administration of the dosage. Any convenient lavage method and system may be employed. Examples of lavage methods and systems that may be employed include, but are not limited to, those described in U.S. Pat. Nos. 6,808,505; 6,419,654; and 7,811,321; the disclosures of which are herein incorporated by reference.

The intra-articularly administered dosage includes a nucleic acid coding sequence for a human IL-1Ra (IL1RN). IL-1Ra is a protein that binds to IL-1 receptors and inhibits the binding of IL-1alpha and IL-1beta thereto. The canonical amino acid sequence of IL-1Ra is:

(SEQ ID NO: 01)

```
        10         20         30         40
MEICRGLRSH LITLLLFLFH SETICRPSGR KSSKMQAFRI

        50         60         70         80
WDVNQKTFYL RNNQLVAGYL QGPNVNLEEK IDVVPIEPHA

        90        100        110        120
LFLGIHGGKM CLSCVKSGDE TRLQLEAVNI IDLSENRKQD

       130        140        150        160
KRFAFIRSDS GPTTSFESAA CPGWFLCTAM EADQPVSLTN

       160        170
EADQPVSLTN MPDEGVMVTK FYFQEDE
```

The human IL-1Ra protein that is encoded by the administered nucleic acid may have the canonical sequence provided above, or a variant thereof. In some instances, the encoded human IL-1Ra that is administered to the human has an amino acid sequence that comprises a region substantially the same as or identical to the sequence appearing as SEQ ID NO:01. By substantially the same as is meant a protein having a region with a sequence that is 60% or greater, such as 75% or greater, such as 90% or greater and including 98% or greater sequence identity with the sequence of SED ID NO:01, as determined by BLAST using default settings.

In addition to the naturally occurring human IL-1Ra proteins, e.g., as described above, proteins that vary from the naturally occurring human IL-1Ra may also be employed in practicing methods of the invention. Different variations may be present, including but not limited to substitution, insertion and/or deletion mutations. Human IL-1Ra polypeptides that may be employed include proteins having an amino acid sequence encoded by an open reading frame (ORF) of an IL-1Ra gene, including the full length IL-1Ra protein and fragments thereof, such as biologically active fragments and/or fragments corresponding to functional domains; and including fusions of the subject polypeptides to other proteins or parts thereof.

Fragments of interest may vary in length, and in some instances are 10 aa or longer, such as 50 aa or longer, and including 100 aa or longer, and in some instances do not exceed 150 aa in length, where a given fragment will have a stretch of amino acids that is substantially the same as or identical to a subsequence found in any of SEQ ID NO:01; where the subsequence may vary in length and in some instances is 10 aa or longer, such as 15 aa or longer, up to 50 aa or even longer.

In some instances, the sequence of the protein encoded by the nucleic acid is the sequence of Kineret, which is:

(SEQ ID NO: 02)

```
MRPSGRKSSK MQAFRIWDVN QKTFYLRNNQ LVAGYLQGPN

VNLEEKIDVV PIEPHALFLG IHGGKMCLSC VKSGDETRLQ

LEAVNITDLS ENRKQDKRFA FIRSDSGPTT SFESAACPGW

FLCTAMEADQ PVSLTNMPDE GVMVTKFYFQ EDE
```

In some instances, the sequence of the protein encoded by the nucleic acid is a functional fragment of the IL-1Ra protein. A functional fragment is understood to mean a part of the IL-1Ra protein that binds to the IL-1 receptor. Such a fragment would include sequences that contact the IL-1 receptor, as described in Schreuder et al., Eur J Biochem. 1995 Feb. 1; 227(3):838-47, Clancy et al. Acta Crystallogr, 1994; D50, 197-201, Vigers et al, J. Biol. Chem., 1994; 269:12874. In some instances, a functional fragment of IL-1Ra includes one or more of the five critical amino acid residues that were identified by Schreuder et al., Nature (1997); 386:194: Trp 16, Gln 20, Tyr 34, Gln 36, and Tyr 147. In some instances, a functional fragment includes amino acid residues 34-39 of SEQ. ID NO. 1, which is known to fit in the cleft between domains 1 and 2 of the IL-1 receptor. These articles are incorporated herein by reference.

In practicing methods such as described herein, any convenient IL-1Ra coding sequence that encodes the desired IL-1Ra protein, such as described above, may be employed. Depending on the desired human IL-1Ra, the nucleic acid coding sequence may vary. Nucleic acids of interest include those encoding the human IL-1Ra proteins provided above. Specific nucleic acids of interest include, but are not limited to those assigned the following NCBI Accession Nos: XM_005263661.4; NM_000577.4; XM_011511121.1; NM_001318914.1; NM_173842.2; NM_173841.2 and NM_173843.2.

In some instances, the nucleic acids have a sequence that is 60% or more, such as 70% or more, 80% or more, 90% or more, including 95% or more, similar to:

(SEQ ID NO: 03)

```
atggaaatctgcagaggcctccgcagtcacctaat

cactctcctcctcttcctgttccattcagagacga

tctgccgaccctctgggagaaaatccagcaagatg

caagccttcagaatctgggatgttaaccagaagac

cttctatctgaggaacaaccaactagttgctggat

acttgcaaggaccaaatgtcaatttagaagaaaag

atagatgtggtacccattgagcctcatgctctgtt

cttgggaatccatggagggaagatgtgcctgtcct

gtgtcaagtctggtgatgagaccagactccagctg

gaggcagttaacatcactgacctgagcgagaacag

aaagcaggacaagcgcttcgccttcatccgctcag

acagtggccccaccaccagttttgagtctgccgcc

tgccccggttggttcctctgcacagcgatggaagc

tgaccagcccgtcagcctcaccaatatgcctgacg

aaggcgtcatggtcaccaaattctacttccaggag

gacgag
```

By nucleic acid composition is meant a composition comprising a sequence of DNA having an open reading frame that encodes a human IL-1Ra protein of interest, i.e., a human IL-1Ra coding sequence, and is capable, under appropriate conditions, of being expressed as a human IL-1Ra protein. Also encompassed in this term are nucleic acids that are homologous, substantially similar or identical to the specific nucleic acids described above. In certain embodiments, sequence similarity between homologues is 20% or higher, such as 25% or higher, and including 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence may be 18 nt long or longer, such as 30 nt long, and may extend to the complete sequence that is being compared.

Algorithms for sequence analysis are known in the art, such as BLAST, described in Altschul et al. (1990), J. Mol. Biol. 215:403-10 (using default settings, i.e. parameters w=4 and T=17). Of particular interest in certain embodiments are nucleic acids of substantially the same length as specific human IL-1Ra nucleic acids mentioned above, where by substantially the same length is meant that any difference in length in terms of number of residues does not exceed about 20%, usually does not exceed about 10% and more usually does not exceed about 5%; and have sequence identity to any of these sequences of at 90% or greater, such as 95% or greater and including 99% or greater over the entire length of the nucleic acid. In some embodiments, the nucleic acids have a sequence that is substantially similar or identical to the above specific sequences. By substantially similar is meant that sequence identity is 60% or greater, such as 75% or greater and including 80, 85, 90, or even 95% or greater. Nucleic acids of interest also include nucleic acids that encode the proteins encoded by the above described nucleic acids, but differ in sequence from the above described nucleic acids due to the degeneracy of the genetic code. The employed coding sequence may or may not be naturally occurring.

In some instances, the coding sequence is one that is codon-optimized. A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein. A codon optimized coding sequence of interest includes:

```
                                       (SEQ ID NO: 04)
ATGGAAATCTGCAGAGGCCTGCGGAGCCACCTGAT

TACCCTGCTGCTGTTCCTGTTCCACAGCGAGACAA

TCTGCCGGCCCAGCGGCCGGAAGTCCAGCAAGATG

CAGGCCTTCCGGATCTGGGACGTGAACCAGAAAAC

CTTCTACCTGCGGAACAACCAGCTGGTGGCCGGAT

ACCTGCAGGGCCCCAACGTGAACCTGGAAGAGAAG

ATCGACGTGGTGCCCATCGAGCCCCACGCCCTGTT

TCTGGGCATCCACGGCGGCAAGATGTGCCTGAGCT

GCGTGAAGTCCGGCGACGAGACAAGACTGCAGCTG

GAAGCCGTGAACATCACCGACCTGAGCGAGAACCG

GAAGCAGGACAAGAGATTCGCCTTCATCAGAAGCG

ACAGCGGCCCCACCACCAGCTTTGAGAGCGCCGCC

TGCCCCGGCTGGTTCCTGTGTACAGCCATGGAAGC

CGACCAGCCCGTGTCCCTGACAAACATGCCCGACG

AGGGCGTGATGGTCACCAAGTTCTATTTTCAAGAA

GATGAGTAA
or

                                       (SEQ ID NO: 05)
ATGGAAATTTGCCGCGGCCTGCGCAGCCATCTGAT

TACCCTGCTGCTGTTTCTGTTTCATAGCGAAACCA

TTTGCCGCCCGAGCGGCCGCAAAAGCAGCAAAATG
```

-continued

```
CAGGCGTTTCGCATTTGGGATGTGAACCAGAAAAC

CTTTTATCTGCGCAACAACCAGCTGGTGGCGGGCT

ATCTGCAGGGCCCGAACGTGAACCTGGAAGAAAAA

ATTGATGTGGTGCCGATTGAACCGCATGCGCTGTT

TCTGGGCATTCATGGCGGCAAAATGTGCCTGAGCT

GCGTGAAAAGCGGCGATGAAACCCGCCTGCAGCTG

GAAGCGGTGAACATTACCGATCTGAGCGAAAACCG

CAAACAGGATAAACGCTTTGCGTTTATTCGCAGCG

ATAGCGGCCCGACCACCAGCTTTGAAAGCGCGGCG

TGCCCGGGCTGGTTTCTGTGCACCGCGATGGAAGC

GGATCAGCCGGTGAGCCTGACCAACATGCCGGATG

AAGGCGTGATGGTGACCAAATTTTATTTTCAGGAA

GATGAA
```

Such a sequence may have the consensus codon sequence:

```
                                       (SEQ ID NO: 06)
ATGGARATHTGYMGNGGNYTNMGNWSNCAYYTNAT

HACNYTNYTNYTNTTYYTNTTYCAYWSNGARACNA

THTGYMGNCCNWSNGGNMGNAARWSNWSNAARATG

CARGCNTTYMGNATHTGGGAYGTNAAYCARAARAC

NTTYTAYYTNMGNAAYAAYCARYTNGTNGCNGGNT

AYYTNCARGGNCCNAAYGTNAAYYTNGARGARAAR

ATHGAYGTNGTNCCNATHGARCCNCAYGCNYTNTT

YYTNGGNATHCAYGGNGGNAARATGTGYYTNWSNT

GYGTNAARWSNGGNGAYGARACNMGNYTNCARYTN

GARGCNGTNAAYATHACNGAYYTNWSNGARAAYMG

NAARCARGAYAARMGNTTYGCNTTYATHMGNWSNG

AYWSNGGNCCNACNACNWSNTTYGARWSNGCNGCN

TGYCCNGGNTGGTTYYTNTGYACNGCNATGGARGC

NGAYCARCCNGTNWSNYTNACNAAYATGCCNGAYG

ARGGNGTNATGGTNACNAARTTYTAYTTYCARGAR

GAYGAR
```

In some embodiments, the nucleic acid sequence contains specific nucleic acids corresponding to r5419598 and r5315952, and in some instances r5419598 "C" (not "T") and rs315952 "C" (not "T").

Nucleic acids as described herein may be present in a vector. Various vectors (e.g., viral vectors, bacterial vectors, or vectors capable of replication in eukaryotic hosts) can be used in accordance with the present invention. Numerous vectors which can replicate in eukaryotic hosts are known in the art and are commercially available. In some instances, such vectors used in accordance with the invention are composed of a bacterial origin of replication and a eukaryotic promoter operably linked to the coding sequence of interest.

Viral vectors used in accordance with the invention may be composed of a viral particle derived from a naturally-occurring virus which has been genetically altered to render the virus replication-defective and to express a recombinant gene of interest in accordance with the invention. Once the virus delivers its genetic material to a cell, it does not generate additional infectious virus but does introduce exogenous recombinant genes into the cell, and in some instances into the genome of the cell. Numerous viral vectors are known in the art, including, for example, retrovirus, adenovirus, helper-dependent adenovirus, adeno-associated virus (AAV), herpes simplex virus (HSV), cytomegalovirus (CMV), vaccinia and poliovirus vectors, lentivirus, poxvirus, hemagglutinatin virus of Japan-liposome (HVJ) complex, Moloney murine leukemia virus, and HIV-based virus. In some instances, the vector that is employed is a non-integrating vector.

In some embodiments, the employed vector is the AAV, which is a small, non-pathogenic dependovirus that has not been associated with human disease, and in the absence of co-infection with a helper virus such as adenovirus or HSV, is unable to replicate. AAV virions, which are non-enveloped and measure 25 nm in diameter, have a genome of 4.9 kB. The AAV genome, which is single-stranded DNA, consists of three open reading frames (ORFs) flanked by two inverted terminal repeats (ITRs), which are 145 bp palendromic sequences that form elaborate hairpin structures and are essential for viral packaging. The first ORF is rep, which encodes 4 proteins involved in viral replication (Rep40, Rep52, Rep68, and Rep72). The second ORF contains cap, which encodes the three structural proteins that make up the icosahedral AAV capsid (VP1, VP2, and VP3). A third ORF, which exists as a nested alternative reading frame in the cap gene, encodes the assembly-activating protein, which localizes AAV capsid proteins to the nucleolus and participates in the process of capsid assembly. AAV has proven to be a safe and efficient vehicle for delivering therapeutic DNA to numerous tissue targets.

Gene delivery vehicles or vectors based on AAV offer many advantages over other viruses. AAV vectors have the ability to infect quiescent cells and give rise to long-term expression of transgenes, and various serotypes exhibit tropisms for different subsets of cells. The delivery efficacy or tropism for different cells depends on a combination of the capsid and the route of administration, which can be either intravenous to expose virus to the body including multiple joints, or intra-articular to expose virus primarily to the injected joint.

AAV vectors may be single stranded (ssAAV), containing a genome of single-stranded DNA of up to 4.7 kilobases.

AAV vectors may also include, for example, self-complementary vectors (scAAV), whose genomes contain both a sense copy of the transgene and a reverse complement, separated by a linker. These two copies are able to anneal and serve as a double stranded template that can be transcribed without the need for generation of any complementary strand by the host cell. scAAV2, scAAV2.5, scAAV5 and scAAV8 are specific examples of such vectors.

Specific AAV vectors finding use in embodiments of the invention include, but are not limited to: AAV1, AAV2, AAV2.5, AAV3, AAV4, AAV5, AAV6, AAV7, AAV8, AAV9, AAV10, AAV11, AAV12 and Anc80.

In some instances, the vector encodes a viral cap gene and has a sequence that is the same as SEQ ID NO:07

```
ATGGCTGCCGATGGTTATCTTCCAGATTGGCTCGA
GGACACTCTCTCTGAAGGAATAAGACAGTGGTGGA
AGCTCAAACCTGGCCCACCACCACCAAAGCCCGCA
GAGCGGCATAAGGACGACAGCAGGGGTCTTGTGCT
TCCTGGGTACAAGTACCTCGGACCCTTCAACGGAC
TCGACAAGGGAGAGCCGGTCAACGAGGCAGACGCC
GCGGCCCTCGAGCACGACAAAGCCTACGACCGGCA
GCTCGACAGCGGAGACAACCCGTACCTCAAGTACA
ACCACGCCGACGCGGAGTTTCAGGAGCGCCTTAAA
GAAGATACGTCTTTTGGGGGCAACCTCGGACGAGC
AGTCTTCCAGGCGAAAAAGAGGGTTCTTGAACCTC
TGGGCCTGGTTGAGGAACCTGTTAAGACGGCTCCG
GGAAAAAAGAGGCCGGTAGAGCACTCTCCTGTGGA
GCCAGACTCCTCCTCGGGAACCGGAAAGGCGGGCC
AGCAGCCTGCAAGAAAAAGATTGAATTTTGGTCAG
ACTGGAGACGCAGACTCAGTACCTGACCCCCAGCC
TCTCGGACAGCCACCAGCAGCCCCCTCTGGTCTGG
GAACTAATACGATGGCTACAGGCAGTGGCGCACCA
ATGGCAGACAATAACGAGGGCGCCGACGGAGTGGG
TAATTCCTCGGGAAATTGGCATTGCGATTCCACAT
GGATGGGCGACAGAGTCATCACCACCAGCACCCGA
ACCTGGGCCCTGCCCACCTACAACAACCACCTCTA
CAAACAAATTTCCAGCCAATCAGGAGCCTCGAACG
ACAATCACTACTTTGGCTACAGCACCCCTTGGGGG
TATTTTGACTTCAACAGATTCCACTGCCACTTTTC
ACCACGTGACTGGCAAAGACTCATCAACAACAACT
GGGGATTCCGACCCAAGAGACTCAACTTCAAGCTC
TTTAACATTCAAGTCAAAGAGGTCACGCAGAATGA
CGGTACGACGACGATTGCCAATAACCTTACCAGCA
CGGTTCAGGTGTTTACTGACTCGGAGTACCAGCTC
CCGTACGTCCTCGGCTCGGCGCATCAAGGATGCCT
CCCGCCGTTCCCAGCAGACGTCTTCATGGTGCCAC
AGTATGGATACCTCACCCTGAACAACGGGAGTCAG
GCAGTAGGACGCTCTTCATTTTACTGCCTGGAGTA
CTTTCCTTCTCAGATGCTGCGTACCGGAAACAACT
TTACCTTCAGCTACACTTTTGAGGACGTTCCTTTC
CACAGCAGCTACGCTCACAGCCAGAGTCTGGACCG
TCTCATGAATCCTCTCATCGACCAGTACCTGTATT
ACTTGAGCAGAACAAACACTCCAAGTGGAACCACC
```

-continued

ACGCAGTCAAGGCTTCAGTTTTCTCAGGCCGGAGC
GAGTGACATTCGGGACCAGTCTAGGAACTGGCTTC
CTGGACCCTGTTACCGCCAGCAGCGAGTATCAAAG
ACATCTGCGGATAACAACAACAGTGAATACTCGTG
GACTGGAGCTACCAAGTACCACCTCAATGGCAGAG
ACTCTCTGGTGAATCCGGGCCCGGCCATGGCAAGC
CACAAGGACGATGAAGAAAAGTTTTTCCTCAGAG
CGGGGTTCTCATCTTTGGGAAGCAAGGCTCAGAGA
AAACAAATGTGGACATTGAAAAGGTCATGATTACA
GACGAAGAGGAAATCAGGACAACCAATCCCGTGGC
TACGGAGCAGTATGGTTCTGTATCTACCAACCTCC
AGAGAGGCAACAGACAAGCAGCTACCGCAGATGTC
AACACACAAGGCGTTCTTCCAGGCATGGTCTGGCA
GGACAGAGATGTGTACCTTCAGGGGCCCATCTGGG
CAAAGATTCCACACACGGACGGACATTTTCACCCC
TCTCCCCTCATGGGTGGATTCGGACTTAAACACCC
TCCTCCACAGATTCTCATCAAGAACACCCCGGTAC
CTGCGAATCCTTCGACCACCTTCAGTGCGGCAAAG
TTTGCTTCCTTCATCACACAGTACTCCACGGGACA
GGTCAGCGTGGAGATCGAGTGGGAGCTGCAGAAGG
AAAACAGCAAACGCTGGAATCCCGAAATTCAGTAC
ACTTCCAACTACAACAAGTCTGTTAATGTGGACTT
TACTGTGGACACTAATGGCGTGTATTCAGAGCCTC
GCCCCATTGGCACCAGATACCTGACTCGTAATCTG
TAA or substantially similar thereto, where by substantially similar is meant that sequence identity is 60% or greater, such as 75% or greater and including 80, 85, 90, or even 95% or greater.

The protein sequence encoded thereby is SEQ ID NO. 08:

MAADGYLPDWLEDTLSEGIRQWWKLKPGPPPPKPA
ERHKDDSRGLVLPGYKYLGPFNGLDKGEPVNEADA
AALEHDKAYDRQLDSGDNPYLKYNHADAEFQERLK
EDTSFGGNLGRAVFQAKKRVLEPLGLVEEPVKTAP
GKKRPVEHSPVEPDSSSGTGKAGQQPARKRLNFGQ
TGDADSVPDPQPLGQPPAAPSGLGTNTMATGSGAP
MADNNEGADGVGNSSGNWHCDSTWMGDRVITTSTR
TWALPTYNNHLYKQISSQSGASNDNHYFGYSTPWG
YFDFNRFHCHFSPRDWQRLINNNWGFRPKRLNFKL
FNIQVKEVTQNDGTTTIANNLTSTVQVFTDSEYQL
PYVLGSAHQGCLPPFPADVFMVPQYGYLTLNNGSQ

-continued

AVGRSSFYCLEYFPSQMLRTGNNFTFSYTFEDVPF
HSSYAHSQSLDRLMNPLIDQYLYYLSRTNTPSGTT
TQSRLQFSQAGASDIRDQSRNWLPGPCYRQQRVSK
TSADNNNSEYSWTGATKYHLNGRDSLVNPGPAMAS
HKDDEEKFFPQSGVLIFGKQGSEKTNVDIEKVMIT
DEEEIRTTNPVATEQYGSVSTNLQRGNRQAATADV
NTQGVLPGMVWQDRDVYLQGPIWAKIPHTDGHFHP
SPLMGGFGLKHPPPQILIKNTPVPANPSTTFSAAK
FASFITQYSTGQVSVEIEWELQKENSKRWNPEIQY
TSNYNKSVNVDFTVDTNGVYSEPRPIGTRYLTRNL

The protein sequence may be substantially similar to SEQ ID NO:08, where by substantially similar is meant that sequence identity is 60% or greater, such as 75% or greater and including 80, 85, 90, or even 95% or greater.

In some cases, the nucleic acid sequence is SEQ ID NO:09:

ATGGCTGCCGATGGTTATCTTCCAGATTGGCTCGA
GGACACTCTCTCTGAAGGAATAAGACAGTGGTGGA
AGCTCAAACCTGGCCCACCACCACCAAAGCCCGCA
GAGCGGCATAAGGACGACAGCAGGGGTCTTGTGCT
TCCTGGGTACAAGTACCTCGGACCCTTCAACGGAC
TCGACAAGGGAGAGCCGGTCAACGAGGCAGACGCC
GCGGCCCTCGAGCACGACAAAGCCTACGACCGGCA
GCTCGACAGCGGAGACAACCCGTACCTCAAGTACA
ACCACGCCGACGCGGAGTTTCAGGAGCGCCTTAAA
GAAGATACGTCTTTTGGGGGCAACCTCGGACGAGC
AGTCTTCCAGGCGAAAAAGAGGGTTCTTGAACCTC
TGGGCCTGGTTGAGGAACCTGTTAAGACGGCTCCG
GGAAAAAAGAGGCCGGTAGAGCACTCTCCTGTGGA
GCCAGACTCCTCCTCGGGAACCGGAAAGGCGGGCC
AGCAGCCTGCAAGAAAAAGATTGAATTTTGGTCAG
ACTGGAGACGCAGACTCAGTACCTGACCCCCAGCC
TCTCGGACAGCCACCAGCAGCCCCCTCTGGTCTGG
GAACTAATACGATGGCTACAGGCAGTGGCGCACCA
ATGGCAGACAATAACGAGGGCGCCGACGGAGTGGG
TAATTCCTCGGGAAATTGGCATTGCGATTCCACAT
GGATGGGCGACAGAGTCATCACCACCAGCACCCGA
ACCTGGGCCCTGCCCACCTACAACAACCACCTCTA
CAAACAAATTTCCAGCGCTTCAACGGGAGCCTCGA
ACGACAATCACTACTTTGGCTACAGCACCCCTTGG
GGGTATTTTGACTTCAACAGATTCCACTGCCACTT

-continued

```
TTCACCACGTGACTGGCAAAGACTCATCAACAACA
ACTGGGGATTCCGACCCAAGAGACTCAACTTCAAG
CTCTTTAACATTCAAGTCAAAGAGGTCACGCAGAA
TGACGGTACGACGACGATTGCCAATAACCTTACCA
GCACGGTTCAGGTGTTTACTGACTCGGAGTACCAG
CTCCCGTACGTCCTCGGCTCGGCGCATCAAGGATG
CCTCCCGCCGTTCCCAGCAGACGTCTTCATGGTGC
CACAGTATGGATACCTCACCCTGAACAACGGGAGT
CAGGCAGTAGGACGCTCTTCATTTTACTGCCTGGA
GTACTTTCCTTCTCAGATGCTGCGTACCGGAAACA
ACTTTACCTTCAGCTACACTTTTGAGGACGTTCCT
TTCCACAGCAGCTACGCTCACAGCCAGAGTCTGGA
CCGTCTCATGAATCCTCTCATCGACCAGTACCTGT
ATTACTTGAGCAGAACAAACACTCCAAGTGGAACC
ACCACGCAGTCAAGGCTTCAGTTTTCTCAGGCCGG
AGCGAGTGACATTCGGGACCAGTCTAGGAACTGGC
TTCCTGGACCCTGTTACCGCCAGCAGCGAGTATCA
AAGACATCTGCGGATAACAACAACAGTGAATACTC
GTGGACTGGAGCTACCAAGTACCACCTCAATGGCA
GAGACTCTCTGGTGAATCCGGGCCCGGCCATGGCA
AGCCACAAGGACGATGAAGAAAAGTTTTTTCCTCA
GAGCGGGGTTCTCATCTTTGGGAAGCAAGGCTCAG
AGAAAACAAATGTGGACATTGAAAAGGTCATGATT
ACAGACGAAGAGGAAATCAGGACAACCAATCCCGT
GGCTACGGAGCAGTATGGTTCTGTATCTACCAACC
TCCAGAGAGGCAACAGACAAGCAGCTACCGCAGAT
GTCAACACACAAGGCGTTCTTCCAGGCATGGTCTG
GCAGGACAGAGATGTGTACCTTCAGGGGCCCATCT
GGGCAAAGATTCCACACACGGACGGACATTTTCAC
CCCTCTCCCCTCATGGGTGGATTCGGACTTAAACA
CCCTCCTCCACAGATTCTCATCAAGAACACCCCGG
TACCTGCGAATCCTTCGACCACCTTCAGTGCGGCA
AAGTTTGCTTCCTTCATCACACAGTACTCCACGGG
ACAGGTCAGCGTGGAGATCGAGTGGGAGCTGCAGA
AGGAAAACAGCAAACGCTGGAATCCCGAAATTCAG
TACACTTCCAACTACGCCAAGTCTGCCAATGTGGA
CTTTACTGTGGACAATAATGGCGTGTATTCAGAGC
CTCGCCCCATTGGCACCAGATACCTGACTCGTAAT
CTGTAA
```

or substantially similar thereto, where by substantially similar is meant that sequence identity is 60% or greater, such as 75% or greater and including 80, 85, 90, or even 95% or greater.

The protein sequence encoded thereby is SEQ ID NO. 10:

```
MAADGYLPDWLEDTLSEGIRQWWKLKPGPPPPKPA
ERHKDDSRGLVLPGYKYLGPFNGLDKGEPVNEADA
AALEHDKAYDRQLDSGDNPYLKYNHADAEFQERLK
EDTSFGGNLGRAVFQAKKRVLEPLGLVEEPVKTAP
GKKRPVEHSPVEPDSSSGTGKAGQQPARKRLNFGQ
TGDADSVPDPQPLGQPPAAPSGLGTNTMATGSGAP
MADNNEGADGVGNSSGNWHCDSTWMGDRVITTSTR
TWALPTYNNHLYKQISSASTGASNDNHYFGYSTPW
GYFDFNRFHCHFSPRDWQRLINNNWGFRPKRLNFK
LFNIQVKEVTQNDGTTTIANNLTSTVQVFTDSEYQ
LPYVLGSAHQGCLPPFPADVFMVPQYGYLTLNNGS
QAVGRSSFYCLEYFPSQMLRTGNNFTFSYTFEDVP
FHSSYAHSQSLDRLMNPLIDQYLYYLSRTNTPSGT
TTQSRLQFSQAGASDIRDQSRNWLPGPCYRQQRVS
KTSADNNNSEYSWTGATKYHLNGRDSLVNPGPAMA
SHKDDEEKFFPQSGVLIFGKQGSEKTNVDIEKVMI
TDEEEIRTTNPVATEQYGSVSTNLQRGNRQAATAD
VNTQGVLPGMVWQDRDVYLQGPIWAKIPHTDGHFH
PSPLMGGFGLKHPPPQILIKNTPVPANPSTTFSAA
KFASFITQYSTGQVSVEIEWELQKENSKRWNPEIQ
YTSNYAKSANVDFTVDNNGVYSEPRPIGTRYLTRN
L
```

The protein sequence may be substantially similar to SEQ ID NO:10, where by substantially similar is meant that sequence identity is 60% or greater, such as 75% or greater and including 80, 85, 90, or even 95% or greater.

Promoters useful in an AAV delivered coding sequence may include, for example constitutively active promoters, such as CMV promoters, β-actin promoters, SV-40 promoters such as 4×GRM6-SV40, etc. Commonly used ubiquitous promoters have been immediate-early cytomegalovirus (CMV) enhancer-promoter and the CAG promoter, which combines the CMV enhancer with the chicken β-actin (CBA) promoter. Promoters having more cell-type specific expression patterns may include, without limitation the regulatory region of the gamma-synuclein gene (SNCG), Nefh promoter, Mcp-1 promoter, etc.

Further details regarding viral vectors that may be employed in embodiments of the invention may be found in U.S. Pat. No. 10,004,788; the disclosure of which is herein incorporated by reference.

In a given dosage employed in the methods described herein, the amount of viral vector present in the dosage may vary. In some cases, the viral vector of the dosage may be measured as pfu (plaque forming units). In some cases, the pfu of recombinant virus, or viral vector of the dosage may range from $10^8$ to $5\times10^{10}$ pfu. In some cases, recombinant viruses of the dosage are $1\times10^8$ or more, $2\times10^8$ or more, $3\times10^8$ or more, $4\times10^8$ or more, $5\times10^8$ or more, $6\times10^8$ or more, $7\times10^8$ or more, $8\times10^8$ or more, $9\times10^8$ or more, $1\times10^9$ or more, $2\times10^9$ or more, $3\times10^9$ or more, $4\times10^9$ or more, $5\times10^9$ or more, $6\times10^9$ or more, $7\times10^9$ or more, $8\times10^9$ or more, $9\times10^9$ or more, $1\times10^{10}$ or more, $2\times10^{10}$ or more, $3\times10^{10}$ or more, $4\times10^{10}$ or more, and $5\times10^{10}$ or more pfu. In some cases, recombinant viruses of this disclosure are $1\times10^8$ or less, $2\times10^8$ or less, $3\times10^8$ or less, $4\times10^8$ or less, $5\times10^8$ or less, $6\times10^8$ or less, $7\times10^8$ or less, $8\times10^8$ or less, $9\times10^8$ or less, $1\times10^9$ or less, $2\times10^9$ or less, $3\times10^9$ or less, $4\times10^9$ or less, $5\times10^9$ or less, $6\times10^9$ or less, $7\times10^9$ or less, $8\times10^9$ or less, $9\times10^9$ or less, $1\times10^{10}$ or less, $2\times10^{10}$ or less, $3\times10^{10}$ or less, $4\times10^{10}$ or less, and $5\times10^{10}$ or less pfu.

In some cases, the viral vector of the employed dosage may be measured as vector genomes. In some cases, dosage includes $1\times10^{10}$ to $3\times10^{12}$ vector genomes. In some cases, recombinant viruses of this disclosure are $1\times10^9$ to $3\times10^{13}$ vector genomes. In some cases, recombinant viruses of this disclosure are $1\times10^8$ to $3\times10^{14}$ vector genomes. In some cases, recombinant viruses of this disclosure are $1\times10^8$ to $2\times10^{13}$ vector genomes. In some cases, recombinant viruses of this disclosure are $1\times10^8$ to $1\times10^{13}$ vector genomes. In some cases, recombinant viruses of this disclosure are $1\times10^{11}$ to $1\times10^{13}$ vector genomes. In some cases, recombinant viruses of this disclosure are $2\times10^{11}$ to $2\times10^{13}$ vector genomes. In some cases, recombinant viruses of the dosage are $1\times10^1$ or more, $1\times10^2$ or more, $1\times10^3$ or more, $1\times10^4$ or more, $1\times10^5$ or more, $1\times10^6$ or more, $1\times10^7$ or more, $1\times10^8$ or more, $1\times10^9$ or more, $1\times10^{10}$ or more, $1\times10^{11}$ or more, $1\times10^{12}$ or more, $1\times10^{13}$ or more, $1\times10^{14}$ or more, $1\times10^{15}$ or more, $1\times10^{16}$ or more, $1\times10^{17}$ or more, and $1\times10^{18}$ or more vector genomes. In some cases, recombinant viruses of the dosage are $1\times10^8$ to $3\times10^{14}$ vector genomes. In some cases, recombinant viruses of the disclosure are $1\times10^1$ or less, $1\times10^2$ or less, $1\times10^3$ or less, $1\times10^4$ or less, $1\times10^5$ or less, $1\times10^6$ or less, $1\times10^7$ or less, $1\times10^8$ or less, $1\times10^9$ or less, $1\times10^{10}$ or less, $1\times10^{11}$ or less, $1\times10^{12}$ or less, $1\times10^{13}$ or less, $1\times10^{14}$ or less, $1\times10^{15}$ or less, $1\times10^{16}$ or less, $1\times10^{17}$ or less, and $1\times10^{18}$ or less vector genomes.

In some cases, the viral vector of the dosage may be measured using multiplicity of infection (MOI). In some cases, MOI may refer to the ratio, or multiple of vector or viral genomes to the cells to which the nucleic may be delivered. In some cases, the MOI may be $1\times10^6$. In some cases, the MOI may be $1\times10^5$-$1\times10^7$. In some cases, the MOI may be $1\times10^4$-$1\times10^8$. In some cases, recombinant viruses of the dosage are $1\times10^1$ or more, $1\times10^2$ or more, $1\times10^3$ or more, $1\times10^4$ or more, $1\times10^5$ or more, $1\times10^6$ or more, $1\times10^7$ or more, $1\times10^8$ or more, $1\times10^9$ or more, $1\times10^{10}$ or more, $1\times10^{11}$ or more, $1\times10^{12}$ or more, $1\times10^{13}$ or more, $1\times10^{14}$ or more, $1\times10^{15}$ or more, $1\times10^{16}$ or more, $1\times10^{17}$ or more, and $1\times10^{18}$ MOI. In some cases, recombinant viruses of this disclosure are $1\times10^8$-$3\times10^{14}$ MOI. In some cases, recombinant viruses of the disclosure are $1\times10^1$ or less, $1\times10^2$ or less, $1\times10^3$ or less, $1\times10^4$ or less, $1\times10^5$ or less, $1\times10^6$ or less, $1\times10^7$ or less, $1\times10^8$ or less, $1\times10^9$ or less, $1\times10^{10}$ or less, $1\times10^{11}$ or less, $1\times10^{12}$ or less, $1\times10^{13}$ or less, $1\times10^{14}$ or less, $1\times10^{15}$ or less, $1\times10^{16}$ or less, $1\times10^{17}$ or less, and $1\times10^{18}$ or less MOI.

Within a given dosage employed in embodiments of the invention, the number of empty viral particles may vary. In some instances, 90% or less, 80% or less, 70% or less, 60% or less, 50% or less, 40% or less, 30% or less, 20% or less, or even 10% or less of the viral particles in the dosage are empty. In some instances, 10% or more, 20% or more, 30% or more, 40% or more, 50% or more, 60% or more, 70% or more, 80% or more, 90% or more of the viral particles in the dosage are full. A variety of methods may be employed to determine the ratio of full to empty particles, wherein is some instances the proportion of empty particles is determined by a method selected from analytical ultracentrifugation (AUC), transmission electron microscopy (TEM), the ratio of genomes (qPCR) to capsid particles (ELISA), or analytical HPLC, and combinations thereof.

The nucleic acid coding sequence may be administered using a non-viral vector, for example, as a nucleic acid-liposome complex formulation. Such complexes comprise a mixture of lipids which bind to genetic material (DNA or RNA), providing a hydrophobic coat which allows the genetic material to be delivered into cells. Liposomes which can be used in accordance with the invention include DOPE (dioleyl phosphatidyl ethanol amine), CUDMEDA (N-(5-cholestrum-3-beta-ol 3-urethanyl)-N',N'-dimethylethylene diamine). When the DNA of interest is introduced using a liposome, in some instances one first determines in vitro the optimal values for the DNA:lipid ratios and the absolute concentrations of DNA and lipid as a function of cell death and transformation efficiency for the particular type of cell to be transformed. These values can then be used in or extrapolated for use in in vivo transformation. The in vitro determinations of these values can be readily carried out using techniques which are well known in the art.

Other non-viral vectors may also be used in accordance with the present invention. These include chemical formulations of nucleic acids coupled to a carrier molecule (e.g., an antibody or a receptor ligand) which facilitates delivery to host cells for the purpose of altering the biological properties of the host cells. By the term "chemical formulations" is meant modifications of nucleic acids to allow coupling of the nucleic acid compounds to a carrier molecule such as a protein or lipid, or derivative thereof. Exemplary protein carrier molecules include antibodies specific to the cells of a targeted secretory gland or receptor ligands, i.e., molecules capable of interacting with receptors associated with a cell of a targeted secretory gland.

In embodiments where the nucleic acid is delivered without the use of a virus (i.e. with a non-viral vector), the amount in the dosage be measured as the quantity of nucleic acid. Generally, any suitable amount of nucleic acid may be used in dosage employed in methods described herein. In some cases, nucleic acid may be 1 pg or more, 10 pg or more, 100 pg or more, 200 pg or more, 300 pg or more, 400 pg or more, 500 pg or more, 600 pg or more, 700 pg or more, 800 pg or more, 900 pg or more, 1 ng or more, 10 ng or more, 100 ng or more, 200 ng or more, 300 ng or more, 400 ng or more, 500 ng or more, 600 ng or more, 700 ng or more, 800 ng or more, 900 ng or more, 1 μg or more, 10 μg or more, 100 μg or more, 200 μg or more, 300 μg or more, 400 μg or more, 500 μg or more, 600 μg or more, 700 μg or more, 800 μg or more, 900 μg or more, 1 mg or more, 10 mg or more, 100 mg or more, 200 mg or more, 300 mg or more, 400 mg or more, 500 mg or more, 600 mg or more, 700 mg or more, 800 mg or more, 900 mg or more, 1 g or more, 2 g or more, 3 g or more, 4 g or more, or 5 g or more. In some cases, nucleic acid may be 1 pg or less, 10 pg or less, 100 pg or less, 1 pg or less, 10 pg or less, 100 pg or less, 200 pg or less, 300 pg or less, 400 pg or less, 500 pg or less, 600 pg or less, 700 pg or less, 800 pg or less, 900 pg or less, 1 ng or less, 10 ng or less, 100 ng or less, 200 ng or less, 300 ng or less, 400 ng or less, 500 ng or less, 600 ng or less, 700 ng or less, 800 ng or less, 900 ng or less, 1 μg or less, 10 μg or less, 100 μg or less, 200 μg or less, 300 μg or less, 400 μg or less, 500 μg or less, 600 μg or less, 700 μg or less, 800 μg or less, 900 μg or less, 1 mg or less, 10 mg or less, 100 mg or less, 200 mg or less, 300 mg or less, 400 mg or less, 500 mg or less, 600 mg or less, 700 mg or less, 800 mg or less, 900 mg or less, 1 g or less, 2 g or less, 3 g or less, 4 g or less, or 5 g or less.

In some instances, the dosage that includes the IL-1Ra encoding nucleic acid also includes a suitable delivery vehicle (i.e., carrier), such as an aqueous delivery vehicle. Delivery vehicles of interest include sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as delivery vehicles. Non-limiting examples of pharmaceutically acceptable delivery vehicles include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropyl-methylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of delivery vehicles include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of delivery vehicles that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade delivery vehicles and excipients are particularly useful for delivery of rAAV particles to human subjects. Such compositions may further optionally include a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

A given dosage employed in methods of the invention may be a formulation containing the encoding nucleic acid, e.g., present in vector such as described above, as well as one or more excipients, carriers, stabilizers or bulking agents, which is suitable for administration to a human patient to achieve a desired diagnostic result or therapeutic or prophylactic effect. For storage stability and convenience of handling, a pharmaceutical composition can be formulated as a lyophilized (i.e. freeze dried) or vacuum dried powder, e.g., the form of a pre-unit dose, which can be reconstituted with saline or water prior to administration to a patient. Alternately, the pharmaceutical composition can be formulated as an aqueous solution. A pharmaceutical composition can contain a proteinaceous active ingredient. Unfortunately, proteins can be very difficult to stabilize, resulting in loss of protein and/or loss of protein activity during the formulation, reconstitution (if required) and during the storage prior to use of a protein containing pharmaceutical composition. Stability problems can occur because of protein denaturation, degradation, dimerization, and/or polymerization. Various excipients, such as albumin and gelatin have been used with differing degrees of success to try and stabilize a protein active ingredient present in a pharmaceutical composition. Additionally, cryoprotectants such as alcohols have been used to reduce protein denaturation under the freezing conditions of lyophilization.

Pharmaceutical compositions suitable for internal use include sterile aqueous solutions or dispersions and sterile powders for the extemporaneous preparation of sterile injectable solutions or dispersion. For intravenous or intra-articular administration, suitable carriers include physiological saline, bacteriostatic water, or phosphate buffered saline (PBS). In all cases, the composition must be sterile and should be fluid to the extent that easy syringe-ability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants such as polysorbates (Tween™), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol (Triton X100™), N, N-dimethyldodecylamine-N-oxide, hexadecyltrimethylammonium bromide (HTAB), polyoxyl 10 lauryl ether, Brij 721™, bile salts (sodium deoxycholate, sodium cholate), pluronic acids (F-68, F-127), polyoxyl castor oil (Cremophor™) nonylphenol ethoxylate (Tergitol™), cyclodextrins and, ethylbenzethonium chloride (Hyamine™). Prevention of the action of microorganisms can be achieved by various antibacterial and antifungal agents, for example, parabens, chlorobutanol, phenol, ascorbic acid, thimerosal, and the like. In some instances, isotonic agents are included, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof The employed dosage may be provided in dosage unit form for ease of administration and uniformity of dosage. Dosage unit form as used herein refers to physically discrete units suited as unitary dosages for the human subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The dosages can be included in a container, pack, or dispenser together with instructions for administration.

In some embodiments, the dosage includes an AAV vector in an aqueous delivery vehicle. In addition to water (such as water for injection), in some instances, the aqueous vehicle includes a buffer, such as but not limited to: citrate buffer, phosphate buffer, acetate buffer, and bicarbonate buffer. In some instances, the delivery vehicle includes a phosphate buffer. When present, the buffer may be provided in any suitable concentration. In some instances, the aqueous delivery vehicle includes a salt, such as but not limited to sodium chloride, potassium chloride, and the like, where in some instances the salt is sodium chloride (NaCl). When present, the salt may be provided in any suitable concentration, wherein in some instances the salt concentration ranges from 100 to 500 mM, such as 125 to 175 mM, e.g., about 150 mM, or such as 300 to 400 mM, e.g., about 350 mM. In some instances, the aqueous delivery vehicle comprises a polyol. Polyols of interest include, but are not limited to: lactose, dextrose, sucrose, sorbitol, mannitol, and the like, where in some embodiments the aqueous delivery vehicle includes sorbitol. While the amount of the polyol may vary, in some instances the amount ranges from 0.1% to 10%, such as 1% to 5%. In some instances, the aqueous delivery vehicle includes a surfactant. Surfactants of interest include, but are not limited to, polymers, such as block copolymers, e.g., polyalkylene glycols, such as poloxamers. Examples of suitable surfactants include, for example, Tergitol® and Triton® surfactants (Union Carbide Chemicals and Plastics, Danbury, Conn.), Pluronic surfactants (BASF) polyoxyethylenesorbitans, for example, TWEEN® surfactants (Atlas Chemical Industries, Wilmington, Del.), polyoxyethylene ethers, for example Brij, pharmaceutically acceptable fatty acid esters, for example, lauryl sulfate and salts thereof (SDS), and like materials. While the amount of the surfactant may vary, in some instances the amount ranges from 0.0001% to 0.1%, such as 0.001% to 0.01%, and in some instances is about 0.001%.

Dosages employed in methods of the invention are safe. By safe is meant that administration of the dosage does not cause serious adverse advents. Serious adverse events are well defined and include: death; life threatening adverse experience; hospitalization, inpatient, new, or prolonged; disability/incapacity; persistent or significant birth defect/abnormal and/or per protocol may be problems/events that in the opinion of the sponsor-investigator may have adversely affected the rights, safety, or welfare of the subjects or others, or substantially compromised the research data.

In practicing methods of the invention, the volume of the dosage that is intra-articularly administered to the human may vary. In some embodiments, the dosage has a volume ranging from 0.25 to 25 ml, such as 0.5 to 15 ml, and including from 2 to 12 ml, where in some instances the amount ranges from 0.5 ml to 1 ml, 1 to 2 ml, 2 to 5 ml or 9 to 11 ml. In some cases, the volume administered may differ based on the joint that is injected. For example, for intra-articular administration to the knee, the dosage may have a volume ranging from 2.0 to 10.0 ml. For intra-articular administration to a spinal joint, the dosage may have a volume ranging from 0.1 to 1.0 ml.

Prior to administration to a human, the dosage may have been stored for a period of time under sub-zero conditions. In some instances, prior to administering the dosage to a human, the dosage has been stored and a temperature less than 0° C., such as less than −10° C., such as less than −20° C., such as less than −30° C., such as less than −40° C., such as less than −50° C., such as less than −60° C. or −65° C., wherein some instances the dosage has been stored at a temperature between −60 to −80° C. In some instances, the dosage has been stored in liquid nitrogen at −196° C. While the period of time for which the dosage may be stored at sub-zero temperatures prior to administration of the dosage to a human may vary, in some instances the period of time is 1 hour or longer, 1 day or longer, such as 1 week or longer, such as 1 month or longer, such as 6 months or longer, such as 1 year or longer, such as 2 years or longer, such as 5 years or longer.

Prior to administration to a human, the dosage may have been stored for a period of time at above-zero sub-room temperature conditions. In some instances, prior to administering the dosage to a human, the dosage has been stored and a temperature that is above zero and below 20° C., such as below 15° C., such as below 10° C., where some instances the dosage been stored at temperature between 2 to 8° C., e.g., at about 4° C., for a period of time prior to administration to the human. While the period of time that the dosage is stored under the above conditions may vary, in some instances the period of time is 1 day or longer, such as 2 days or longer, such as 3 days or longer, such as 4 days or longer, such as 5 days or longer, such as 6 days or longer, such as 7 days or longer, such as 8 days or longer, such as 9 days or longer, such as 10 days or longer, such as 11 days or longer, such as 12 days or longer, such as 13 days or longer, such as 14 days or longer prior to the administering to the human, where in some instances the dosage is stored under these conditions immediately prior to administering the dosage to a human.

In some instances, the potency of the dosage is measured in a cell culture system prior to administration. Potency can be measured, for example, by transfecting or transducing a cell with the vector or nucleic acid sequence encoding IL-1Ra. The resulting conditioned media is then applied to a cell system that is responsive to IL-1a or IL-1β, and the responsiveness is measured and quantified. An example of such a cell culture system is HEK-Blue™ IL-1β cells. In some instances, the potency of the dosage that is measured after storage is at least 95%, at least 90%, at least 80%, at least 70%, at least 60%, at least 50%, at least 40%, at least 30%, at least 20% or at least 10% of its original activity after manufacture.

In some instances, the human to which the dosage is administered in practicing methods of the invention is an adult. The age of the adult may vary, and in embodiments is generally 18 years or older, such as 25 years or older, 30 years or older, 35 years or older, 40 years or older, 45 years or older, 50 years old or older, e.g., 60 years old or older, 70 years old or older, 80 years old or older, and sometimes no older than 100 years old, such as 90 years old, i.e., between the ages of about 20 and 100, e.g., 20, 25, 30, 35, 40, 45, 50, 55, 60, 65, 70, 75, 80, 85 or 90 years old.

As summarized above, the human to which the dosage is intra-articularly administered is one suffering from or may be predicted to suffer from OA. The particular OA may vary, wherein some instances the OA is selected from the group consisting OA of the hand, knee, hip, shoulder, ankle, elbow, temporomandibular joint, and spine, and combinations thereof. In some instances, the OA is OA of the knee. In some instances, OA is OA of the hip. In some instances, the OA is OA of the hand. In some instances, the OA is OA of the spine, for example a facet joint or intravertebral disc joint.

In some instances, the OA is early OA, moderate OA or severe OA.

In some instances, the human has been diagnosed as having OA, where in some instances the method includes diagnosing the human as having OA. The OA of the human may have been assessed or evaluated using one or more protocols. In some instances, the OA has been assessed at least in part using an imaging protocol. A variety of different imaging protocols may be employed in assessing OA. In some instances, a radiographic (i.e., X-ray) protocol is employed.

For example, the structural progression of OA may be assessed on plain radiographic views by measuring the joint space width (JSW) and/or joint space narrowing (JSN) over a period of time. (Altman et al.: Osteoarthritis Cartilage 1996, 4:217-243.) OA progression is associated with accelerated cartilage degradation leading to JSN, painful joint disruption, and functional compromise. OA disease progression may be measured on a Kellgren-Lawrence Grading Scale ("KL scale") to measure occurrence and severity of OA in human subjects. Grade 0 means the joints of a human subject is normal. Grade 1 means a human subject has doubtful narrowing of joint space and possible osteophytic lipping. Grade 2 means a human subject has definite osteophytes, definite narrowing of joint space. Grade 3 means a human subject has moderate multiple osteophytes, definite narrowing of joint space, some sclerosis and possible deformity of bone contour. Grade 4 means a human subject has large osteophytes, marked narrowing of joint space, severe sclerosis and definite deformity of bone contour. In some instances, the OA of the human has been assigned a Kellgren-Lawrence score of 2, 3 or 4. In some instances, the human has been assigned a Kellgren-Lawrence score of 2 or 3.

In some instances, the OA is assessed using a magnetic resonance imaging (MRI) protocol, e.g., to identify bone marrow lesions. Bone marrow lesions (or edemas) are very strongly associated with knee arthritis pain (Felson et al., "The association of bone marrow lesions with pain in knee osteoarthritis." Ann Intern Med. 2001 Apr. 3; 134(7):541-9) and disease progression (Felson et al., "Bone marrow edema and its relation to progression of knee osteoarthritis." Ann Intern Med. 2003 Sep. 2; 139(5 Pt 1):330-6). See also U.S. Pat. No. 6,564,083 to Stevens, which describes a method of identifying in a patient having joint pain the susceptibility of the patient to developing progressive OA or loss of joint space, by determining the presence or absence of bone marrow edema about or of the joint. The determination may be made through the use of MRI. See also U.S. Published Patent Application 20170202520 the disclosure of which is herein incorporated by reference.

In some instances, the OA has been assessed using a subjective protocol, such as a pain reporting protocol. In some instances a pain assessment scale such as the Visual Analog Scale ("VAS") is employed, where a patient is asked to indicate a point on a 100 millimeter line, having a left anchor of no pain and a right anchor of worst possible pain, corresponding to their degree of pain. In some instances a Likert score, wherein a patient is asked to categorize their pain according to none/mild/moderate/severe/extreme, or a numerical scale from 0 (no pain) to 10 (worst possible pain) is used. Additional subjective approaches that may be employed in assessing the OA include, but are not limited to: the Western Ontario and MacMaster Universities Osteoarthritis Index (WOMAC) pain questionnaire; the Knee injury and Osteoarthritis Outcome Score (KOOS) questionnaire; the McGill Pain Questionnaire; the 36-Item Short Form Health Survey (SF-36); and the like.

In some embodiments, the OA has been assessed at least in part using a biomarker evaluation protocol. Such assessment may include measuring, observing or detecting the presence or activity in a biomarker. In various embodiments, the biomarker is a molecule that indicates presence or extent of the pain in the individual. The assessment may include measuring, observing or detecting a change in concentration or activity of the biomarker over a period of time may be employed. For example, the assessment may include observing a reduction in amount of the biomarker. Alternatively, the change is an increase in amount of the biomarker. In some instances, the measuring, observing or detecting includes using an assay, a questionnaire, a strip, a well, a gel, a detector, an indicator, a dye, an imager, and a slide.

In various embodiments, the biomarker includes at least one compound selected from the group consisting of: a carbohydrate; a peptide; a protein; and a genetic material, e.g., DNA or RNA (collectively referred to as "nucleic acid"). In various embodiments of the method, the biomarker includes a growth factor, an interleukin (IL), an osteoinductive factor, an interferon, a tumor necrosis factor (TNF), a steroid, a proteoglycan, a collagen or collagen fragment, a fiber, a serum protein, an immunoglobulin, a hormone.

In various embodiments of the method, the biomarker includes at least one biomarker selected from the group consisting of: a cell; a peptide or protein expressed by the cell; or a molecule that binds to the cell. For example, the biomarker is located in the serum or the cartilage of the individual. In various embodiments of the method, the biomarker comprises at least one selected from the group consisting of: a high-sensitivity C-reactive protein (hsCRP); a matrix metallopeptidase (MMP; for example MMP-9); a vascular endothelial growth factor (VEGF), a MMP degradation product for example a MMP degradation product of type I, II, or III collagen (C1M, C2M, C3M); a C-reactive protein (CRPM), CTX-I, CTX-II, TIINE, creatinine, and a vimentin (for example a citrullinated and MMP-degraded vimentin, VICM). In some instances, the biomarker evaluation protocol comprises assaying a biomarker selected from the group consisting of IL-1, TNF-α, IL-1Ra, COMP, CTXII, sGAG, NTX-1, MMP1, MMP3 and MMP9, and combinations thereof.

Measuring, observing or detecting the biomarker in various embodiments comprises obtaining a sample from the individual. For example, the sample is selected from: a cell, a fluid, and a tissue. In various embodiments of the method, the fluid is at least one selected from the group consisting of: serum, plasma, synovial fluid, saliva, and urine. In various embodiments of the method, the cell or the tissue is at least one selected from the group consisting of: vascular; epithelial; endothelial; dermal; connective; muscular; neuronal; soft tissue including cartilage and collagen; bone; bone marrow; joint tissue; and an articular joint. For example, the sample is collected after administering the binding protein and the biomarker is measured, observed or detected. These biomarker data are then compared to a suitable control sample or predetermined standard.

In any of the above methods, the biological sample or samples may comprise any one of synovial fluid, whole blood, blood plasma, serum, urine, and saliva. In some instances, the protein level determination assay one or more polypeptides is employed. In some embodiments, the protein level is measured using a method selected from the group consisting of: LUMINEX, ELISA, immunoassay, mass spectrometry, high performance liquid chromatography, two-dimensional electrophoresis, Western blotting, protein microarray, and antibody microarray.

In other embodiments, a nucleic acid expression assay may be employed. The expression levels (or expression profile) can be then determined using any convenient method, where such methods include, but are not limited to, polymerase-based assays such as qPRC, RT-PCR (e.g., TAQMAN or SYBR Green), hybridization-based assays such as DNA microarray analysis, flap-endonuclease-based assays (e.g., INVADER), and direct mRNA capture (QUANTIGENE or HYBRID CAPTURE (Digene)). See, for example, US 2010/0190173 for descriptions of representative methods that can be used to determine expression levels.

In some instances, peripheral blood leukocytes (PBL) are employed as a source of nucleic acid to be used in assays. PBLs can be obtained from an individual in the form of a Peripheral Blood Mononuclear Cell (PBMC) sample. PBMCs are a mixture of monocytes and lymphocytes, and there are a number of known methods for isolating PBMCs from whole blood. While any suitable method may be employed, in one embodiment, PBMCs are isolated from whole blood samples using density gradient centrifugation. Alternatively, PBL may be further isolated from whole blood or PBMCs to yield a cell subpopulation, such as a population of lymphocytes (e.g., T-lymphocytes or subpopulation thereof). Examples for isolating such sub-populations include cell sorting or cell-capturing using antibodies to particular cell-specific markers. In another embodiment, PBL can be obtained from whole blood using the PAXgene kit (Qiagen).

RNA can be extracted from the collected cells (e.g., from PBMC or PBL samples or from blood plasma) using any convenient protocol. For example, RNA may be purified from cells using a variety of standard procedures as described, for example, in RNA Methodologies, A laboratory guide for isolation and characterization, 2nd edition, 1998, Robert E. Farrell, Jr., Ed., Academic Press. In addition, various commercial products are available for RNA isolation. As would be understood by those skilled in the art, total RNA or polyA+ RNA may be used for preparing gene expression profiles.

In some embodiments, the biomarker evaluation protocol includes a genotyping assay. The term "genotype or genotyping" means the combination of alleles that determines a specific trait of an individual or the particular alleles at specified loci present in an organism. The genotyping assay may genotype one or more genes, where genes of interest include, but are not limited to: IL1A, IL1B, and IL1RN, where the gene accession numbers for these genes are X03833, X04500, and X64532, respectively. In some instances, the genotyping assay includes genotyping an interleukin-1 receptor antagonist (URN) gene. In some instances, the genotyping comprises assaying for the presence of a polymorphism. The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long. In some instances, the genotyping includes assessing a single nucleotide polymorphism (SNP), including assay 2 or more SNPs, e.g., 3 or more SNPs. While the SNPs may vary, as desired, in some instances the SNPs are IL1RN SNPs, such as but not limited to: r5419598, r5315952, or rs9005. In some instances, the genotyping assay is a haplotyping assay. The term "haplotype" as used herein is intended to refer to a set of alleles that are inherited together as a group (are in linkage disequilibrium) at statistically significant levels ($P_{corr}$<0.05). Haplotype patterns can be identified by detecting any of the component alleles using any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Amplification methods that may be employed include those selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected, for example, from within the IL-1Ra gene loci, either flanking the marker of interest (as required for PCR amplification) or directly overlapping the marker (as in ASO hybridization). In some embodiments, the sample is hybridized with a set of primers, which hybridize 5' and 3' in a sense or antisense sequence to the disease associated allele, and is subjected to a PCR amplification. In some embodiments, an allelic discrimination assay such as a TaqMan SNP genotyping assay, may be used, e.g., as described in Teh L-K, Lee T-Y, Tan JAMA et al. (2015); *Int J Lab Hematol* 37(1):79-89. Genotyping assays that may be employed in embodiments of methods of the invention are further described in published United States Patent Application Nos. 20180223362; 20160340734; 20160032386; 20150203917; 20150072364; the disclosures of which are herein incorporated by reference.

In some instances, the human to which the dosage is administered in practicing methods of the invention is one that has at least one copy of the haplotype TTG at rs419598/rs315952/rs9005. In some instances, the human has two copies of haplotype TTG at rs419598/rs315952/rs9005. In another instance, the human has one copy of haplotype TTG at rs419598/rs315952/rs9005, and zero copies of haplotype CTA at rs419598/rs315952/rs9005.

In some instances, the human has persistently suffered from one or more symptoms of OA despite undertaking a non-steroidal anti-inflammatory drug (NSAID) treatment regimen. A NSAID treatment regimen is a treatment regimen that includes administration of one or more NSAIDs, where examples of NSAIDs include, but are not limited to: acetaminophen (Tylenol), Aspirin (brand names include Bayer, Bufferin, and Ecotrin, St. Joseph); Ibuprofen (Advil, Motrin); Naproxen (Aleve, Anaprox DS, Naprosyn); Celecoxib (Celebrex); and the like. In yet other embodiments, the human that is treated according to embodiments of the invention is one that has undergone or is undergoing an NSAID treatment regimen, e.g., where the human has been administered an NSAID treatment regimen for 1 to 60 months.

In some embodiments, the human that is administered the dosage in accordance with the invention is one that has failed a minimum of two conservative therapies for the OA. Conservative therapies included, but are not limited to: activity modification, weight loss, physical therapy, steroid therapy, non-steroidal anti-inflammatory therapy, injection therapy (such as hyaluronic acid, steroids, Zilretta, and the like), and combinations thereof. For example, the human may have failed a three-month trial of two conservative therapies for the OA.

In some instances, the human that is administered the dosage in accordance with the invention is one that is not undergoing anti-rheumatic disease medication therapy. Anti-rheumatic disease medication therapy is a treatment regimen that includes administration of a Disease-modifying anti-rheumatic drug (DMARD). DMARD is a category of otherwise unrelated drugs defined by their use in rheumatoid arthritis to slow down disease progression. DMARDs include, but are not limited to: Abatacept, adalimumab, anakinra, azathioprine, chloroquine (anti-malarial), ciclosporin (Cyclosporin A), D-penicillamine, etanercept, golimumab, gold salts (sodium aurothiomalate, auranofin), hydroxychloroquine, infliximab, leflunomide, methotrexate (MTX), minocycline, rituximab, sulfasalazine (SSZ), tocilizumab, tofacitinib, and the like.

In various embodiments, the method further comprises observing a reduction in an indicium of the OA. In various embodiments, the method further comprises observing a reduction in a condition associated with the OA. For example, the indicium or condition is presence of an osteophyte, bone sclerosis, effusion, joint swelling, synovitis, synovial hypertrophy and hyperplasia, angiogenesis, inflammation, stiffness, joint space narrowing, or pain associated with the OA.

In various embodiments, the method further includes observing or detecting a modulation (e.g., reduction or increase) in presence or activity of a biomarker. In various embodiments, the biomarker indicates presence or extent of the OA. For example, the biomarker corresponds to presence of inflammation. In various embodiments of the method, the biomarker comprises at least one selected from the group consisting of: a carbohydrate; a peptide; a protein; and a genetic material. For example, the genetic material comprises DNA or RNA.

The biomarker comprises in various embodiments at least one selected from the group consisting of: a cell; a peptide or protein expressed by the cell; or a molecule that binds to the cell. In various embodiments of the method, the biomarker comprises a monocyte, a macrophage, B cells, T cells, a cytokine, (e.g., TNF, and IL-1Ra), a growth factor, an interleukin (e.g., IL-4, IL-6, IL-10, and IL-13), an osteoinductive factor, an interferon, a tumor necrosis factor, a steroid, a proteoglycan, a fiber, a collagen or collagen fragment, a serum protein, an immunoglobulin, or a hormone. In various embodiments of the method, the biomarker comprises at least one selected from the group consisting of: C-reactive protein (CRP); a matrix metallopeptidase (MMP; for example MMP-9); a vascular endothelial growth factor (VEGF), a MMP degradation product for example MMP degradation product of type I, II, or III collagen (C1M, C2M, C3M); a prostaglandin, nitric oxide, a disintegrin and metalloproteinase with thrombospondin motifs (ADAMTS), an adipokine, an endothelial growth factor (EGF), a bone morphogenetic protein (BMP), a nerve growth factor (NGF), a substance P, an inducible nitric oxide synthase (iNOS), CTX-I, CTX-II, TIINE, creatinine, and a vimentin (for example a citrullinated and MMP-degraded vimentin; VICM). In various embodiments, the biomarker comprises a local tissue degradation biomarker.

In various embodiments herein, observing or detecting the biomarker comprises obtaining a sample from the individual. In various embodiments, the sample is selected from: a cell, a fluid, and a tissue. For example, the fluid is at least one selected from: serum, plasma, synovial fluid, saliva, and urine. The cell or the tissue comprises for example at least one type selected from: vascular; epithelial; endothelial; dermal; connective; muscular; neuronal; soft tissue for example cartilage, synovium, capsule and collagen; bone; bone marrow; joint tissue; and an articular joint. For example, the biomarker is detected using an assay, a computer, or a probe. For example, the probe is a molecular probe that detects the presence of the biomarker. In an embodiment, the binding protein reduces the OA and/or modulates (e.g., reduces and increases) expression and/or activity of the biomarker by at least about 1%, 3%, 5%, 7% 10%, 15%, 20%, 25%, 30%, 35%, 40%, 45%, 50%, 55%, 60%, 65%, 70%, 75%, 80%, 85%, 90%, 95%, 99% or more.

In various embodiments of the method, the method reduces the OA in at least one metric or criteria from the group consisting of: Western Ontario and McMaster Universities Arthritis Index (WOMAC), The Knee injury and Osteoarthritis Outcome Score (KOOS), International Knee Documentation Committee (IKDC) score, Whole-Organ Magnetic Imaging Score (WORMS), Intermittent and Constant Osteoarthritis Pain (ICOAP) score; 11-point Numeric Rating Score (NRS) score, and the individual's assessment (for example a questionnaire or a patient's global assessment). In various embodiments, observing or evaluating is performed over a period of time selected from the group consisting of: hours, days, weeks, and months. In various embodiments, observing or evaluating determines that the method does not produce adverse effects in the individual. In various embodiments of the method, observing or evaluating determines that the method is at least one characteristic selected from the group consisting of: efficacious, therapeutic, safe, and producing beneficial biochemical and/or effects in the individual. In an embodiment, the method reduces the OA and/or modulates the metric by at least about 1%, 3%, 5%, 7% 10%, 15%, 20%, 25%, 30%, 35%, 40%, 45%, 50%, 55%, 60%, 65%, 70%, 75%, 80%, 85%, 90%, 95%, 99% or more.

The method in various embodiments further comprises observing or detecting a reduction in an indicium of the pain. For example, the pain condition is associated with knee OA or erosive hand OA. In various embodiments of the method, the pain is nociceptive pain associated with OA. For example, the pain is mechanical nociceptive pain associated with OA.

In some instances, embodiments of the method result in persistent amelioration of one or more symptoms of the OA, such as pain. In some instances, the method results in a reduction in pain, e.g., as determined using one or more above described assessment protocols, such as a visual analog scale. Where reduction in pain is determined using a visual analog scale, the magnitude of pain reduction is manifested by a movement along of the scale of 10% or more of the length of scale, such as 20% or more of the length of scale, including 30% or more of the length of scale, as well as 40% or more, including 50% or more, of the length of scale. Where reduction of pain is determined using a Likert scale, such as WOMAC or KOOS, the magnitude of pain reduction is manifested by a movement of 0.5 units or more, 1 units or more, 1.5 units or more, 2 units or more, 3 units or more, 4 units or more, or 5 units or more. Where reduction of pain is determined using a numerical scale, such as the WOMAC pain 0-50 subscale, the magnitude of pain reduction is manifested by a movement of 1 units or more, 2 units or more, 3 units or more, 4 units or more, 5 units or more, 6 units or more, or 7 units or more. While the duration of symptom, e.g., pain, amelioration may vary, in some instances the persistent amelioration lasts for 3 months or longer, such as 6 months or longer, including 9 months or longer, e.g., 12 months or longer, 18 months or longer, 24 months or longer, 30 months or longer, 36 months or longer, and in some instances the persistent amelioration lasts for 3 to 36 months.

In some instances, the method results in a synovial fluid human IL-1Ra concentration ranging from 0.1 ng/ml to 400 ng/ml, such as 1 ng/ml to 400 ng/ml, such as 10 ng/ml to 100 ng/ml or 20 ng/ml to 50 ng/ml, for a period of 1 to 36 months or longer following administration, such as 1 month, 3 months, 6 months, 12 months, 18 months, 24 months, 30 months, 36 months following administration to the human. Synovial fluid human IL-1Ra concentration may be determined using any convenient protocol, e.g., by taking a sample of synovial fluid and assays for human IL-1Ra protein therein, e.g., using the assays described above.

In some instances, the method further results in a modification of joint structure of the human, such as reduction in tissue degeneration and/or reduction of joint space narrowing. As such, methods may result in restoration, at least to some extent, of joint structure of the human, where restoration means a return, a least in part, to the structure of a health joint of a non-osteoarthritic human. In some instances, the method results in a preservation of joint structure of the human, e.g., so that the joint structure does not further change but is stabilized. In such instances, the modification or preservation may be determined by an imaging protocol, such as the radiographic and/or magnetic resonance imaging protocols described above.

In some instances, the method results in substantially no cell-mediated immune response, i.e., an immune response produced when sensitized T cells attack foreign antigens and secrete lymphokines that initiate the body's humoral immune response. In yet other instances, the method may result in a cell-mediated immune response. In such instances, the cell-mediated immune response includes a CD8+ cytotoxic T-cell response. Where desired, the cell-mediated immune response is evaluated by an immunoassay, such as an ELISpot assay.

In some instances, the human produces substantially no antibodies to the encoded IL-1Ra. In yet other embodiments, the human produces substantially no antibodies to the vector that includes a coding sequence for IL-1Ra, such as the vectors described above.

In yet other instances, the method results in production of antibodies to the encoded IL-1Ra and/or vector comprising a coding sequence therefor. For example, the method may result in the production of antibodies to the encoded IL-1Ra. In some instances, the method may result in the production of antibodies to a vector comprising a coding sequence for IL-1Ra, such as the vectors described above.

In some instances, the human that is treated in accordance with methods of the invention is one that has pre-existing antibodies to a vector that includes a coding sequence for IL-1Ra, such as described above. In some instances, the human may be one that does not have pre-existing antibodies to a vector that includes a coding sequence for IL-1Ra at a titer greater than 1:5, at a titer greater than 1:10, at a titer greater than 1:20, at a titer greater than 1:40, at a titer greater than 1:80, at a titer greater than 1:100, at a titer greater than 1:160, at a titer greater than 1:320, at a titer greater than 1:640. In some instances, the injected joint is treated with joint lavage prior to injection. In some instances, this is performed to decrease neutralizing antibodies in the joint to be injected.

In some instances, the method further includes administering a second OA therapy to the human. As such, dosages of the invention can be administered to a subject alone or in combination with an additional, i.e., second, active agent or composition. As such, in some cases, the subject method further comprises administering to the subject at least one additional therapy. Any convenient therapy may be utilized. Examples of additional OA therapies that may be employed include, but are not limited to: acetaminophen therapy, NSAID therapy, opiate therapy, glucocorticoid therapy, hyaluronic acid therapy, stem cell therapy, autologous blood product therapy, such as platelet rich plasma therapy, and combinations thereof. In some cases, this could be a steroid such as triamcinolone, triamcinolone acetonide, including a sustained release version such as Zilretta®. In some cases, the additional therapy could be FGF-18 (sprifermin) or Lorecivivint (SM04690).

Kits & Systems

Also provided are kits and systems that find use in practicing embodiments of the methods, such as those described as described above. The term "system" as employed herein refers to a collection of two or more different active agents, present in a single composition or in disparate compositions, that are brought together for the purpose of practicing the subject methods. The term "kit" refers to a packaged active agent or agents.

For example, kits and systems for practicing the subject methods may include one or more pharmaceutical formulations, e.g., dosages in the form of unit doses or pre-unit doses, such as described above. In certain embodiments the kits may include a single pharmaceutical composition, present as one or more unit doses. In some instances, the kits include a pre-unit dose that includes an AAV vector comprising a coding sequence for a human IL-1Ra and a diluent (e.g., water for injection, saline, etc.) where combination of the diluent with the pre-unit dose produces a safe pharmaceutical unit dose comprising an AAV vector comprising a coding sequence for a human IL-1Ra and an aqueous delivery vehicle, e.g., as described above. In some embodiments, the kits may include two or more separate pharmaceutical compositions, each containing a different active compound, such as a unit dose of a dosage as described above as well as a DMARD and/or NSAID.

In certain embodiments, the kit includes a subject device and a packaging configured to hold the reagent device. The packaging may be a sealed packaging, e.g., a water vapor-resistant container, optionally under an air-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.).

The kits may further include devices that find use in intra-articular delivery of the provided dosage. Examples of such devices include, but are not limited to: syringes, needles, etc.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

As can be appreciated from the disclosure provided above, embodiments of the present disclosure have a wide variety of applications. Accordingly, the examples presented herein are offered for illustration purposes and are not intended to be construed as a limitation on the embodiments of the present disclosure in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

I. A Phase I Study Evaluating the Safety of Intra-Articular Sc-rAAV2.51L-1Ra in Subjects with Moderate Osteoarthritis of the Knee A. Overview An open-label, uncontrolled, phase I trial of the safety and tolerability of a new drug sc-rAAV2.51L-1Ra when introduced by intra-articular injection into human knee joints with moderate OA is conducted. Subjects are screened for suitability and interested, qualified subjects are consented and offered participation in the trial. Once consent has been obtained, baseline values are be established and qualifying subjects receive a single, intra-articular injection of sc-rAAV2.5IL-1Ra into the affected knee joint as out patients. After a 2-hour period of observation, subjects are allowed to return home and asked to return the following day so that the injected knee joint can be examined for signs of inflammation and swelling. Subjects undergo clinical evaluation at 1 day, 1 week, 2 weeks, 1 month, 3 months, 6 months and 12 months (final visit) after injection of sc-rAAV2.51L-1Ra.

B. Study Details

1. Patient Inclusion and Exclusion Criteria a. Inclusion Criteria

- Age 18-65 years
- Gender: both males and females
- Target disease: Moderate OA of the knee
- Persistent symptoms, despite standard NSAID
- Normal limits for the following:
  - i. Complete blood count
  - ii. Prothrombin Time, Activated partial thromboplastin time
  - iii. Blood chemistry (Glucose, Na, K, Cl, $CO_2$, BUN, creatinine, Ca, $PO_4$, magnesium, uric acid)
  - iv. Liver function tests (amylase, total bilirubin, alkaline phosphate, GGT, AST, ALT, total protein, albumin)
- Able and willing to return to the Mayo Clinic for follow-up visits, as required by this study
- Able undergo MRI of the knee
- Subjects should be able to give appropriate consent or have an appropriate representative available to do so.
- Potential subjects should have failed a three-month trial of a minimum of two conservative therapies before being considered for this trial. These conservative therapies include: activity modification, weight loss, physical therapy, and anti-inflammatory or injection therapy.

b. Exclusion Criteria

- Pregnant, or currently breast-feeding
- Ongoing infectious disease including HIV, HTLV, hepatitis, syphilis or tuberculosis positive
- Individuals who have OA as part of another syndrome (e.g. Ehler's Danlos, Stickler syndrome, etc.)
- Systemic, rheumatic or inflammatory disease of the knee or chondrocalcinosis, hemochromatosis, inflammatory arthritis, arthropathy of the knee associated with juxta-articular Paget's disease of the femur or tibia, ochronosis, hemophilic arthropathy, infectious arthritis, Charcot's knee joint, villonodular synovitis, and synovial chondromatosis.
- Clinically significant cardiovascular, renal, hepatic, endocrine disease, diabetes, cancer, autoimmune diseases; a serious infection or major operation within 30 days of enrollment; a history of psychiatric disease or recent history of alcoholism or drug addiction.
- Currently taking immunosuppressant medications
- Anticipated major surgery during the study period.
- Individuals involved in another protocol, or have been treated under one within the last 3 months.
- Intra-articular therapy in the index knee within the previous 6 months.
- Surgery to the target knee within 6 months prior to screening.
- Surgery to other weight bearing joints if it will interfere with knee assessments
- Prior articular transplant procedures
- Prior reconstruction surgery to the target knee within 12 months
- X-ray findings of acute fractures
- Known severe loss of bone density, and/or severe bone or joint deformity in the target knee.
- Knee pain associated with patella-femoral arthritis or chondromalacia in the target knee.
- Significant target knee infection or overlying skin disorder/infection within the previous 6 months prior to study enrollment
- Require cane or other assistive device for walking
- Symptomatic OA of the hips, spine or ankle if it would interfere with the evaluation of the target knee,
- History of documented nerve damage in the affected limb, or vascular insufficiency,
- Condition requiring use of systemic steroids,
- Coagulation disorder.
- Patients with unstable knees
- Temperature above 99.5° F.
- Elevated liver transaminases
- Identification as a member of a vulnerable population.
- BMI greater than 40.
- History of allergy to local anesthetics
- Currently taking anti-rheumatic disease medication (including methotrexate or other antimetabolites) within the 3 months prior to entry in the study.

2. Drug Product

Sc-rAAV2.5IL-1Ra is a self-complementing, recombinant adeno-associated virus, serotype 2.5, containing the full coding sequence of human interleukin-1 receptor antagonist (IL-1Ra). The coding sequence has been codon-optimized for greater expression of IL-1Ra. The final product formulation consists of a sterile solution of sc-rAAV2.51L-1Ra in phosphate buffered saline with 5% sorbitol and 350 mM NaCl.

The drug is initially provided frozen on dry ice. At the time of dispensing, the product will be thawed per patient, drawn up for injection and delivered to the area where it is needed.

3. Treatment Regimen

Each subject receives a single, intra-articular 10.0 ml injection of the drug product under ultrasound guidance. This will take less than 1 minute. If an effusion is present, it will be aspirated prior to injection of the drug, which will take an additional 1-2 minutes.

Patients will receive low ($10^{11}$ vg), medium ($10^{12}$ vg) or high ($10^{13}$ vg) dose of the drug on a first-come, first-served basis. This is a dose-escalation study, so the lowest dose will be administered first. There will be a gap of 2 weeks between subjects at any given dose level, by which time the previous subject will have undergone at least 2 follow-up visits to confirm absence of severe adverse events. There will be a gap of 1 month between cohorts. This ensures that each subject at a lower dose level will have undergone at least 4 follow-up visits before the dose is escalated to the next level.

A total of 9 subjects participate in this dose-escalation trial, with 3 cohorts of 3 subjects receiving low ($10^{11}$ vg), medium ($10^{12}$ vg) and high ($10^{13}$ vg) doses of the study drug.

4. Study Procedures a. Visit 1 (day 0)

Eligible subjects are identified and consented into the study

Subjects undergo history and physical examination

Vital signs

Concurrent medications reviewed

Blood draw

HIV, HTLV, hepatitis, syphilis or tuberculosis testing

Consented subjects undergo X-ray of the knee to determine Kellgren-Lawrence score, unless they have had a suitable X-ray within the past 3 months.

Women of child-bearing age undergo pregnancy test b. Visit 2 (day 7)

Subjects meeting entry criteria undergo baseline screening:

Vital signs

Administration of WOMAC questionnaire

Determination of pain severity using VAS

Concurrent medications reviewed

MRI of index knee joint

Blood draw

Urinalysis

Arthrocentesis

Injection of sc-rAAV2.5IL-1Ra c. Visit 3 (day 8)

Physical examination of the injected knee for pain or swelling.

Vital signs

Blood draw

Urinalysis

4. Visit 4 (week 2)

Physical examination

Vital signs

Concurrent medications reviewed

Blood draw

Urinalysis

Determination of pain severity using VAS

5. Visit 5 (week 3)

Physical examination

Vital signs

Concurrent medications reviewed

Blood draw

Urinalysis

Determination of pain severity using VAS

6. Visit 6 (week 5)

Physical examination

Vital signs

Concurrent medications reviewed

Blood draw

Urinalysis

Arthrocentesis

Administration of WOMAC questionnaire

Determination of pain severity using VAS

7. Visit 7 (week 13)

Physical examination

Vital signs

Concurrent medications reviewed

Blood draw

Urinalysis

Arthrocentesis

Administration of WOMAC questionnaire

Determination of pain severity using VAS

8. Visit 8 (week 27)

Physical examination

Vital signs

Concurrent medications reviewed

Blood draw

Urinalysis

Arthrocentesis

Administration of WOMAC questionnaire

Determination of pain severity using VAS

X-ray

9. Visit 9 (Week 53) this is the Final Visit

Physical examination

Vital signs

Concurrent medications reviewed

Blood draw

Urinalysis

Arthrocentesis

Administration of WOMAC questionnaire

Determination of pain severity using VAS

MRI

X-ray

10. Summary

TABLE 1

Schedule of Events.
SCHEDULE OF EVENTS

| Study Activity | Day 0 | Day 7 (+/−1 day) | Day 8 (1 day post Day 7) | Week 2 (+/−2 days) | Week 3 (+/−2 days) | Week 5 (+/−3 days) | Week 13 (+/−7 days) | Week 27 (+/−14 days) | Week 53 (+/−30 days) |
|---|---|---|---|---|---|---|---|---|---|
| Study Agent | | X | | | | | | | |
| Informed Consent | X | | | | | | | | |
| History | X | | | | | | | | |
| Physical exam | X | | X | X | X | X | X | X | X |

TABLE 1-continued

| Schedule of Events. SCHEDULE OF EVENTS | | | | | | | | | |
|---|---|---|---|---|---|---|---|---|---|
| Study Activity | Day 0 | Day 7 (+/−1 day) | Day 8 (1 day post Day 7) | Week 2 (+/−2 days) | Week 3 (+/−2 days) | Week 5 (+/−3 days) | Week 13 (+/−7 days) | Week 27 (+/−14 days) | Week 53 (+/−30 days) |
| Vital Signs[A] | X | X | X | X | X | X | X | X | X |
| Concurrent meds | X | X | X | X | X | X | X | X | X |
| X-ray | X | | | | | | | X | X |
| MRI of knee | | X | | | | | | | X |
| Arthrocentesis[B] | | X | | | | X | X | X | X |
| CBC, chemistry, PT[C] | X | | | X | X | X | X | X | X |
| Liver Function[D] | X | | | X | X | X | X | X | X |
| HIV, Hep, Syph, TB | X | | | | | | | | |
| Urinalysis[E] | | X | X | X | X | X | X | X | X |
| Special Lab Assays[F] | | X | X* | X | X | X | X | X | X |
| WOMAC | | X | | | | X | X | X | X |
| VAS | | X | | X | X | X | X | X | X |
| B-HCG[G] | X | | | | | | | | |
| Adverse event evaluation | ←----------X----------→ | | | | | | | | |

[A]Vial signs - Temperature, Ht, Wt, BP, HR and Resp

[B]Synovial fluid will be aspirated. If sufficient volume, fluids will be assayed for IL-1Ra; hsIL-1β; IL-1α, IL-6; IL-8; FGF-2; TGF-β; TNF-α; hsCRP; neutralizing antibodies to AAV2.5, antibodies to the transgene/IL-1 receptor antagonist

[C]Complete blood count, Blood chemistry (Glucose, Na, K, Cl, $CO_2$, BUN, creatinine, Ca, $PO_4$, magnesium, uric acid), Prothrombin Time, Activated partial thromboplastin time

[D]Liver function tests (amylase, total bilirubin, alkaline phosphate, GGT, AST, ALT, total protein, albumin)

[E]Urinalysis - assay for viral genomes

[F]Includes serum IL-1Ra; hsIL-1β; IL-1α, IL-6; IL-8; FGF-2; TGF-β; TNF-α; hsCRP; neutralizing antibodies to IL-1Ra and AAV2.5, antibodies to the transgene/IL-1 receptor antagonist; cell-mediated responses to AAV2.5; DNA from peripheral blood and assay for viral genomes (*Day 8 will test for viral genomes only)

[G]Pregnancy test (women of childbearing age)

C. Results

1. Safety

The above protocol is observed to be safe as defined as the absence of serious adverse events. An adverse event is defined as an untoward or undesirable experience associated with the use of a medical product (i.e. drug, device, biologic) in a patient or research subject. Serious adverse events are well defined and include:

- death
- life threatening adverse experience
- hospitalization
- inpatient, new, or prolonged; disability/incapacity
- persistent or significant birth defect/anomaly and/or per protocol may be problems/events that in the opinion of the sponsor-investigator may have adversely affected the rights, safety, or welfare of the subjects or others, or substantially compromised the research data.

2. Additional Observations

- Expression of IL-1Ra is observed, as assessed by measuring the concentration of IL-1Ra in synovial fluid aspirated from the injected joint
- The protocol is determined to have a beneficial effect on disease activity, measured by the Western Ontario McMaster Universities OA Index (WOMAC)
- The protocol is determined to reduce pain, as measured by a Visual Analog Scale (VAS)
- The protocol is determined to have a restorative effect on joint structure, as determined by magnetic resonance imaging (MRI)

II. Second Formulation

The above protocol is performed with a dosage formulation containing a sterile solution of sc-rAAV2.5IL-1Ra (described above) in TMN buffered formulation (20 mM Tris, 1 mM $MgCl_2$, 200 mM NaCl) and 0.001% (w/v poloxamer 188)). The dosage formulation is observed to be safe and effective.

III. Third Formulation

The above protocol is performed with a 2 mL dosage formulation containing a sterile solution of sc-rAAV2.5IL-1Ra (described above) in TMN buffered formulation (20 mM Tris, 1 mM $MgCl_2$, 200 mM NaCl) and 0.001% (w/v poloxamer 188)). The dosage formulation is observed to be safe and effective.

IV. A Phase 2b, Randomized, Double-Blind, Placebo-Controlled Study to Evaluate the Efficacy, Safety, and Pharmacokinetic Properties of Single Intra-Articular Injections of Sc-rAAV2.51L-1Ra Gene Therapy in Subjects with Osteoarthritis of the Knee A. Overview A Phase 2b, randomized, placebo-controlled, subject and investigator blinded, parallel 3 group study is performed to evaluate the efficacy, safety, tolerability, PK and PD profiles, and immunogenicity of sc-rAAV2.51L-1Ra in subjects with knee OA. The study is conducted in 4-8 clinical centers in the US.

The study is comprised of a screening period, baseline measurement, treatment day, short-term follow-up and long-term follow-up periods. After providing informed consent, subjects undergo screening assessments to determine eligibility, including X-ray, NAb test, and genetic test. Subjects are 18 to 80 years of age inclusive, at the time of signing the informed consent. Subjects have OA in at least one knee diagnosed clinically and confirmed using X-ray with a Kellgren Lawrence (KL) score of 2-3 (the "target knee") and symptoms affecting the target knee present for at least 6 months. Subjects have IL1RN genotype TTG-2 or TTG-1/

CTA-0 at r5419598/r5315952/rs9005. Subjects have persistent symptoms of knee OA, despite failure of a three-month trial of a minimum of two 2 conservative therapies. These conservative therapies include: activity modification, weight loss, physical therapy, and anti-inflammatory, or injection of hyaluronic acid or steroids. Subjects have a WOMAC pain score >25 (on 50 point numerical rating scale). The screening visit occurs between 14 and 42 days prior to study administration (Day −42 to −14) so that adequate time is allowed for radiologist reading of X-ray and completion of laboratory tests prior to randomization.

After eligibility is confirmed and prior to study intervention administration (around Day −7), eligible subjects are randomized in 1:1:1 ratio to 1 of 3 treatment groups as specified in Table 1.

TABLE 2

| Study Treatment Groups | | | | |
|---|---|---|---|---|
| Treatment Group | N | Treatment | Dose Regimen | Route of administration |
| 1 | 41 | GNSC-001 | 1 × $10^{12}$ vector genomes (vg) | Intra-articular injection to the affected knee |
| 2 | 41 | GNSC-001 | 1 × $10^{13}$ vg | |
| 3 | 41 | Placebo | Placebo | |

Randomization is based upon a pre-determined randomization schedule based upon a computer-generated schedule. Randomization is stratified by the following parameters:

a. Genetics: TTG-2 vs. TTG-1/CTA-0 b. Baseline pain assessment: <32 vs. 32 WOMAC pain subscale c. Baseline KL score: 2 vs. 3

On Day 1 (Baseline), randomized subjects receive a single intra-articular injection of study intervention into the affected target knee. Subjects remain in clinic for 2 hours following study intervention for safety monitoring and evaluation. Subjects are contacted by phone within 24 hours post study intervention administration. Subjects are followed for 52 weeks initial follow-up plus 104 weeks long term follow-up, for a total of 156 weeks follow up.

Throughout the study, assessments will be done as specified in the following Schedule of Activities (SoA).

TABLE 3

Study Schedule of Activities (SOA)

| | Procedure | | | | | | | | | | |
|---|---|---|---|---|---|---|---|---|---|---|---|
| | Screening | | | Short-Term Follow-up Period | | | | Long-Term Follow-up Period | | | |
| | (Day −42 to Day −14) | Day −7 | Baseline Day 1 | Week 2 | Week 12 | Week 26 | Week 52 | Week 78 | Week 104 | Week 130 | Week 156 EOS/ET |
| | Visit number | | | | | | | | | | |
| | SCR | R | BSL | 4 | 5 | 6 | 7 | 8 | 9 | 10 | 11 |
| | Visit window (days) | | | | | | | | | | |
| | | ±5 | | ±3 | ±7 | | | | ±21 | | |
| Informed consent | X | | | | | | | | | | |
| Demographics | X | | | | | | | | | | |
| Medical history | X | | | | | | | | | | |
| Pregnancy test (WOCBP only) | Serum | | Urine | | | | | | | | |
| Eligibility criteria | X | | | | | | | | | | |
| DNA test (saliva sample collection) | X | | | | | | | | | | |
| Height and Weight | X | | | | | | | | | | |
| Physical exam (abbreviated) | X | | X | | X | X | X | X | X | X | X |
| Vital signs (temperature, heart rate and blood pressure) | X | | X | X | X | X | X | X | X | X | X |
| Randomization | | X | | | | | | | | | |
| Study intervention administration | | | X | | | | | | | | |
| Telephone check-up 24 hours post injection | | | X | | | | | | | | |
| WOMAC questionnaire | X | | X | | X | X | X | X | X | X | X |
| EQ-5D-5L questionnaire | | | X | | | | X | | X | | X |
| Function assessments[1] | | | X | | | X | X | X | X | X | X |
| Ultrasound of target knee[2] | | | X | | X | X | X | X | X | X | X |
| X-ray (fixed flexion) | X | | | | | | X | | X | | X |

TABLE 4

List of Biomarkers Assessments
Serum/Plasma: hsCRP, CCL2/CCL4, hPRO-C2, C10C, IL-1Ra, huARGS, PGE2, 15-HETE
Peripheral Blood Lymphocyte mRNA: IL1alpha, IL1beta, TNFalpha, Cox-2; 18-S (control) and GAPDH (control)
Synovial fluid: IL-1Ra, PGE2, Fibronectin, huARGS, 15-HETE, CCL2/CCL4, C3M, hPro-C2, FGF-18, sVAP-1, S100A8 & A9, IL1alpha, IL1beta, IL-6, IL-8
Urine (fasting): uCTX-II, uCTX-1alpha

| | Screening | | | Short-Term Follow-up Period | | | | Long-Term Follow-up Period | | | |
|---|---|---|---|---|---|---|---|---|---|---|---|
| Procedure | (Day −42 to Day −14) | Day −7 | Baseline Day 1 | Week 2 | Week 12 | Week 26 | Week 52 | Week 78 | Week 104 | Week 130 | Week 156 EOS/ET |
| Magnetic resonance imaging of knee | | | X | | | | X | | X | | X |
| Clinical laboratory tests[3] | X | | X | | X | | X | | X | | X |
| Immunogenicity blood collection[4] | X | | X | X | X | X | X | | X | | X |
| PD blood collection | | | X | | X | X | X | | X | | X |
| Synovial fluid collection | | | X | | X | X | X | (X) | (X) | (X) | (X) |
| Urine collection (fasting - first urine) | | | X | | | | X | | X | | X |
| Biodistribution | | | X | X | X | X | X | | X | | X |
| Adverse events | X | | X | X | X | X | X | (X) | (X) | (X) | (X) |
| Concomitant medication/therapy | X | | X | X | X | X | X | X | X | X | X |
| Subject diary for rescue medications (electronic) | | | | X | X | X | X | X | X | X | X |

Abbreviations: European Quality of Life 5 dimensions 5 levels (EQ-5D-5L); End of study (EOS), Early termination (ET); pharmacodynamic (PD); pharmacokinetic (PK); visual analogue scale (VAS); Western Ontario and McMaster Universities Osteoarthritis Index (WOMAC); women of childbearing potential (WOCBP)
Notes:
1. Function assessments include (a) 30-second Chair Stand Test; (b) 40-meter Fast-paced Walk Test; (c) Stair Climb Tests.
2. At the baseline visit, injection to be given under ultrasound guidance. Routine ultrasound evaluation to be performed and signs of inflammation/synovitis to be recorded in CRF at baseline and week 12, 26, 52, 78, 104, 130, 156/EOS.
[3]Routine safety laboratory includes hematology and clinical chemistry.
[4]Immunogenicity tests will include anti-AAV antibodies (NAb and TAb), ELISpot for anti-AAV T-cells (PBMCs).

B. Results

1. Safety

The above protocol is observed to be safe as defined as the absence of serious adverse events. An adverse event is defined as an untoward or undesirable experience associated with the use of a medical product (i.e. drug, device, biologic) in a patient or research subject. Serious adverse events are well defined and include:

death life threatening adverse experience hospitalization inpatient, new, or prolonged; disability/incapacity persistent or significant birth defect/anomaly and/or per protocol may be problems/events that in the opinion of the sponsor-investigator may have adversely affected the rights, safety, or welfare of the subjects or others, or substantially compromised the research data.

2. Additional Observations

Expression of IL-1Ra is observed, as assessed by measuring the concentration of IL-1Ra in synovial fluid aspirated from the injected joint The protocol is determined to have a beneficial effect on disease activity, measured by the Western Ontario McMaster Universities OA Index (WOMAC)

The protocol is determined to reduce pain, as measured by a Visual Analog Scale (VAS)

The protocol is determined to have a restorative effect on joint structure, as determined by magnetic resonance imaging (MRI)

V. Measurement of Potency Using a Bioassay

To measure IL-1Ra bio-activity, HEK-Blue™ IL-1β cells were seeded in 96 well plates at 50,000 cells/well, resuspended in 150 μL of either media alone, media containing 20 ng/mL recombinant IL-1Ra, or media from cells transduced with AAV-IL-1Ra. In triplicates, cells were either exposed to no IL-1β or recombinant IL-1β (0.001 ng/mL, 0.01 ng/mL or 0.1 ng/mL). Twelve hours later, each sample was harvested and heat-inactivated at 50° C. for 30 minutes. This step denatures any endogenous background alkaline phosphatase, leaving only the heat-stable secreted embryonic alkaline phosphatase secreted by the HEK-Blue cells in response to IL-1. Following heat-inactivation, 50 μl of each sample was added to 150 μl of QUANTI-blue detection culture medium in new wells. This detection culture medium contains a substrate that turns a purple/blue color when hydrolyzed by alkaline phosphatase. Following three hours of incubation, the alkaline phosphatase was quantified using a spectrophotometer at 650 nm.

Notwithstanding the appended claims, the disclosure is also defined by the following clauses:

1. A method for treating a human suffering from osteoarthritis, the method comprising:

intra-articularly administering a dosage comprising a nucleic acid coding sequence for a human interleukin-1 receptor antagonist (IL-1Ra) to the human to treat the human suffering from osteoarthritis.

2. The method according to Clause 1, wherein the coding sequence comprises a naturally occurring coding sequence.

3. The method according to Clause 1, wherein the coding sequence comprises a non-naturally occurring coding sequence.

4. The method according to Clause 3, wherein the coding sequence comprises a codon-optimized coding sequence.

5. The method according to Clause 4, wherein the coding sequence comprises a sequence that is 95% or more identical to SEQ ID NOS:04 or 05.

6. The method according to any of the preceding clauses, wherein the coding sequence is present in a vector.

7. The method according to Clause 6, wherein the vector is a viral vector.

8. The method according to Clause 7, wherein the viral vector is non-integrating viral vector.

9. The method according to Clause 8, wherein the non-integrating viral vector is an adeno-associated virus (AAV) vector.

10. The method according to Clause 9, wherein the AAV vector is selected from the group consisting of AAV1, AAV2, AAV2.5, AAV3, AAV4, AAV5, AAV6, AAV7, AAV8, AAV9, AAV10, AAV11, AAV12 and Anc80.

11. The method according to Clause 10, wherein the AAV vector is an AAV2.5 vector.

12. The method according to Clause 11, wherein the vector has a cap protein having a sequence that is 95% or more identical to SEQ ID NO: 08 or 010.

13. The method according to any of Clauses 9 to 12, wherein the AAV vector is a self-complementary AAV (scAAV) vector.

14. The method according to any of Clauses 7 to 13, wherein 90% or less of the viral particles in the dosage are empty.

15. The method according to Clause 14, wherein 80% or less of the viral particles in the dosage are empty.

16. The method according to Clause 15, wherein 70% or less of the viral particles in the dosage are empty.

17. The method according to Clause 16, wherein 60% or less of the viral particles in the dosage are empty.

18. The method according to Clause 17, wherein 50% or less of the viral particles in the dosage are empty.

19. The method according to Clause 18, wherein 40% or less of the viral particles in the dosage are empty.

20. The method according to Clause 19, wherein 30% or less of the viral particles in the dosage are empty.

21. The method according to Clause 20, wherein 20% or less of the viral particles in the dosage are empty.

22. The method according to Clause 21, wherein 10% or less of the viral particles in the dosage are empty.

23. The method according to any of Clauses 7 to 12, wherein 10% or more of the viral particles in the dosage are full.

24. The method according to Clause 23, wherein 20% or more of the viral particles in the dosage are full.

25. The method according to Clause 24, wherein 30% or more of the viral particles in the dosage are full.

26. The method according to Clause 25, wherein 40% or more of the viral particles in the dosage are full.

27. The method according to Clause 26, wherein 50% or more of the viral particles in the dosage are full.

28. The method according to Clause 27, wherein 60% or more of the viral particles in the dosage are full.

29. The method according to Clause 28, wherein 70% or more of the viral particles in the dosage are full.

30. The method according to Clause 29, wherein 80% or more of the viral particles in the dosage are full.

31. The method according to Clause 30, wherein 90% or more of the viral particles in the dosage are full.

32. The method according to any of Clauses 14 to 31, wherein the proportion of empty particles is determined by a method selected from analytical ultracentrifugation (AUC), transmission electron microscopy (TEM), the ratio of genomes (qPCR) to capsid particles (ELISA), or analytical HPLC.

33. The method according to any of the preceding clauses, wherein the coding sequence is operatively linked to a promoter.

34. The method according to Clause 33, wherein the promoter is a non-human promoter.

35. The method according to Clause 34, wherein the promoter is a viral promoter.

36. The method according to Clause 35, wherein the promoter is a cytomegalovirus immediate early promoter.

37. The method according to any of the preceding clauses, wherein the dosage comprises an aqueous delivery vehicle.

38. The method according to Clause 37, wherein the aqueous delivery vehicle comprises a buffer.

39. The method according to Clause 38, wherein the buffer comprises a phosphate buffer.

40. The method according to any of the Clauses 37 to 39, wherein the aqueous delivery vehicle comprises a salt.

41. The method according to Clause 40, wherein the salt is NaCl.

42. The method according to any of Clauses 37 to 41, wherein the aqueous delivery vehicle comprises a polyol.

43. The method according to Clause 42, wherein the polyol comprises a sugar alcohol.

44. The method according to Clause 43, wherein the sugar alcohol is sorbitol.

45. The method of according to any of Clauses 37 to 44, wherein the aqueous delivery vehicle comprises a surfactant.

46. The method according to Clause 45, wherein the surfactant is a polymer.

47. The method according to Clause 46, wherein the polymer is block copolymer.

48. The method according to Clause 47, wherein the block copolymer is a polyalkylene glycol.

49. The method according to Clause 48, wherein the polyalkylene glycol is a poloxamer.

50. The method according to any of Clauses 7 to 49, wherein the dosage comprises from $1\times10^8$ to $2\times10^{13}$ viral vector genomes.

51. The method according to Clause 50, wherein the dosage comprises from $1\times10^8$ to $1\times10^{13}$ viral vector genomes.

52. The method according to Clause 51, wherein the dosage comprises from $1\times10^{11}$ to $1\times10^{13}$ viral vector genomes.

53. The method according to Clause 50, wherein the dosage comprises from $2\times10^{11}$ to $2\times10^{13}$ viral vector genomes.

54. The method according to any of the preceding clauses, wherein the dosage has a volume ranging from 0.25 to 25 ml.

55. The method according to Clause 54, wherein the dosage has a volume ranging from 2 to 12 ml.

56. The method according to Clause 55, wherein the dosage has a volume ranging from 2 to 5 ml.

57. The method according to Clause 56, wherein the dosage has a volume ranging from 9 to 11 ml.

58. The method according to any of the preceding clauses, wherein the dosage has been stored at a temperature between −60 to −80° C. for 1 day or longer prior to the administering to the human.

59. The method according to Clause 58, wherein the dosage has been stored at a temperature between −60 to −80° C. for 1 week or longer prior to the administering to the human.

60. The method according to Clause 59, wherein the dosage has been stored at a temperature between −60 to −80° C. for 1 month or longer prior to the administering to the human.

61. The method according to Clause 60, wherein the dosage has been stored at a temperature between −60 to −80° C. for 6 months or longer prior to the administering to the human.

62. The method according to Clause 61, wherein the dosage has been stored at a temperature between −60 to −80° C. for 1 year or longer prior to the administering to the human.

63. The method according to Clause 62, wherein the dosage has been stored at a temperature between −60 to −80° C. for 2 years or longer prior to the administering to the human.

64. The method according to Clause 63, wherein the dosage has been stored at a temperature between −60 to −80° C. for 5 years or longer prior to the administering to the human.

65. The method according to any of Clauses 1 to 57, wherein the dosage has been stored at a temperature ranging from 2 to 8° C. for 1 day or longer prior to the administering to the human.

66. The method according to Clause 65, wherein the dosage has been stored at a temperature ranging from 2 to 8° C. for 2 days or longer prior to the administering to the human.

67. The method according to Clause 66, wherein the dosage has been stored at a temperature ranging from 2 to 8° C. for 3 days or longer prior to the administering to the human.

68. The method according to Clause 67, wherein the dosage has been stored at a temperature ranging from 2 to 8° C. for 4 days or longer prior to the administering to the human.

69. The method according to Clause 68, wherein the dosage has been stored at a temperature ranging from 2 to 8° C. for 5 days or longer prior to the administering to the human.

70. The method according to Clause 69, wherein the dosage has been stored at a temperature ranging from 2 to 8° C. for 6 days or longer prior to the administering to the human.

71. The method according to Clause 70, wherein the dosage has been stored at a temperature ranging from 2 to 8° C. for 7 days or longer prior to the administering to the human.

72. The method according to Clause 71, wherein the dosage has been stored at a temperature ranging from 2 to 8° C. for 8 days or longer prior to the administering to the human.

73. The method according to Clause 72, wherein the dosage has been stored at a temperature ranging from 2 to 8° C. for 9 days or longer prior to the administering to the human.

74. The method according to Clause 73, wherein the dosage has been stored at a temperature ranging from 2 to 8° C. for 10 days or longer prior to the administering to the human.

75. The method according to Clause 74, wherein the dosage has been stored at a temperature ranging from 2 to 8° C. for 11 days or longer prior to the administering to the human.

76. The method according to Clause 75, wherein the dosage has been stored at a temperature ranging from 2 to 8° C. for 12 days or longer prior to the administering to the human.

77. The method according to Clause 76, wherein the dosage has been stored at a temperature ranging from 2 to 8° C. for 13 days or longer prior to the administering to the human.

78. The method according to Clause 77, wherein the dosage has been stored at a temperature ranging from 2 to 8° C. for 14 days or longer prior to the administering to the human.

79. The method according to any of the preceding clauses, wherein the human is an adult.

80. The method according to any of the preceding clauses, wherein the osteoarthritis is selected from the group consisting osteoarthritis of the hand, knee, hip, shoulder, ankle, elbow, temporomandibular joint, and spine, and combinations thereof.

81. The method according to Clause 80, wherein the osteoarthritis is osteoarthritis of the knee.

82. The method according to Clause 81, wherein the osteoarthritis is moderate osteoarthritis.

83. The method according to any of the preceding clauses, wherein the osteoarthritis has been assessed at least in part using an imaging protocol.

84. The method according to Clause 83, wherein the imaging protocol comprises an X-ray protocol.

85. The method according to Clause 84, wherein the assessing comprises employing a scale.

86. The method according to Clause 85, wherein the scale comprises the Kellgren-Lawrence scale.

87. The method according to Clause 86, wherein the osteoarthritis has been assigned a Kellgren-Lawrence score of 2, 3 or 4.

88. The method according to Clause 87, wherein the osteoarthritis has been assigned a Kellgren-Lawrence score of 2.

89. The method according to Clause 87, wherein the osteoarthritis has been assigned a Kellgren-Lawrence score of 3.

90. The method according to Clause 83, wherein the imaging protocol comprises a magnetic resonance imaging (MRI) protocol.

91. The method according to any of the preceding clauses, wherein the osteoarthritis has been assessed at least in part using a pain reporting protocol.

92. The method according to Clause 91, wherein the pain reporting protocol comprises a visual analog scale.

93. The method according to any of the preceding clauses, wherein the osteoarthritis has been assessed at least in part using a biomarker evaluation protocol.

94. The method according to Clause 93, wherein the biomarker evaluation protocol comprises assaying a biomarker selected from the group consisting of IL-1, TNF-α, IL-1Ra, COMP, CTXII, sGAG, NTX-1, MMP1, MMP3 and MMP9, and combinations thereof.

95. The method according to any of Clauses 93 to 94, wherein the biomarker evaluation protocol comprises a nucleic acid expression assay.

96. The method according to any of Clauses 93 to 95, wherein the biomarker evaluation protocol comprises a protein level determination assay.

97. The method according to any of Clauses 93 to 96, wherein the biomarker evaluation protocol comprises a genotyping assay.

98. The method according to Clause 97, wherein the genotyping assay comprises genotyping an interleukin 1 receptor antagonist (IL1RN) gene.

99. The method according to Clause 98, wherein the genotyping comprises single nucleotide polymorphism (SNP) analysis.

100. The method according to Clause 99, wherein the SNP analysis comprises assessing 2 or more SNPs.

101. The method according to Clause 100, wherein the 2 or more SNPs comprise r5419598, r5315952, or rs9005.

102. The method according to Clause 101, wherein the genotyping assay comprises a haplotyping assay.

103. The method according to any of Clauses 99 to 102, wherein the human is r5419598 TT, rs315952 TT and rs9005 GG.

104. The method according to any of Clauses 93 to 103, wherein the biomarker evaluation protocol comprises assaying a blood sample.

105. The method according to Clause 104, wherein the blood sample comprises a peripheral blood sample.

106. The method according to Clause 105, wherein the peripheral blood sample comprises peripheral blood leukocytes (PBL).

107. The method according to any of the preceding clauses, wherein the human has persistently suffered from one or more symptoms of osteoarthritis despite undertaking an NSAID treatment regimen.

108. The method according to Clause 107, wherein the human has been administered an NSAID treatment regimen for 1 to 60 months.

109. The method according to any of the preceding clauses, wherein the human has failed a three-month trial of a minimum of two conservative therapies for the osteoarthritis.

110. The method according to Clause 109, wherein the conservative therapies are selected from the group consisting of activity modification, weight loss, physical therapy, steroid therapy, non-steroidal anti-inflammatory therapy, injection therapy, and combinations thereof.

111. The method according to any of the preceding clauses, wherein the human is not undergoing anti-rheumatic disease medication therapy.

112. The method according to any of the preceding clauses, wherein the method results in persistent amelioration of one or more symptoms of the osteoarthritis.

113. The method according to Clause 112, wherein the one or more symptoms comprises pain.

114. The method according to Clause 113, wherein the amelioration comprises a reduction in pain.

115. The method according to Clause 114, wherein the reduction in pain is determined using a visual analog scale.

116. The method according to Clause 115, wherein the magnitude of pain reduction is manifested by a movement along of the scale of 10% or more of the length of scale.

117. The method according to Clause 116, wherein the magnitude of pain reduction is manifested by a movement along of the scale of 20% or more of the length of scale.

118. The method according to Clause 117, wherein the magnitude of pain reduction is manifested by a movement along of the scale of 30% or more of the length of scale.

119. The method according to Clause 118, wherein the magnitude of pain reduction is manifested by a movement along of the scale of 40% or more of the length of scale.

120. The method according to any of Clauses 112 to 119, wherein the persistent amelioration lasts for 3 months or longer.

121. The method according to Clause 120, wherein the persistent amelioration lasts for 6 months or longer.

122. The method according to Clause 121, wherein the persistent amelioration lasts for 9 months or longer.

123. The method according to Clause 122, wherein the persistent amelioration lasts for 12 months or longer.

124. The method according to Clause 123, wherein the persistent amelioration lasts for 18 months or longer.

125. The method according to Clause 124, wherein the persistent amelioration lasts for 24 months or longer.

126. The method according to Clause 125, wherein the persistent amelioration lasts for 30 months or longer.

127. The method according to Clause 126, wherein the persistent amelioration lasts for 36 months or longer.

128. The method according to Clause 120, wherein the persistent amelioration lasts for 3 to 36 months.

129. The method according to any of the preceding clauses, wherein the method results in a synovial fluid IL-1Ra concentration ranging from 0.1 ng/ml to 400 ng/ml for a period of 1 to 36 months or longer following administration.

130. The method according to any of the preceding clauses, wherein the method further results in a modification of joint structure of the human.

131. The method according to any of the preceding clauses, wherein the method further results in a preservation of joint structure of the human.

132. The method according to Clauses 130 or 131, wherein the modification or preservation is determined by an imaging protocol.

133. The method according to Clause 132, wherein the imaging protocol comprises magnetic resonance imaging.

134. The method of according to Clause 133, wherein the imaging protocol comprises a radiographic protocol.

135. The method according to any of the preceding clauses, wherein the method results in substantially no cell-mediated immune response.

136. The method according to any of the preceding clauses, wherein the method results in a cell-mediated immune response.

137. The method according to Clause 136, wherein the cell-mediated immune response comprises a CD8+ cytotoxic T-cell response.

138. The method according to Clauses 136 or 137, wherein the cell-mediated immune response is evaluated by an immunoassay.

139. The method according to Clause 138, wherein the immunoassay is an ELISpot assay.

140. The method of any of the preceding clauses, wherein human produces substantially no antibodies to the encoded IL-1Ra.

141. The method of any of the preceding clauses, wherein human produces substantially no antibodies to the vector comprising a coding sequence for IL-1Ra.

142. The method according to any of Clauses 1 to 139, wherein the method results in production of antibodies to the encoded IL-1Ra or vector comprising a coding sequence therefor.

143. The method according to Clause 142, wherein the method results in the production of antibodies to the encoded IL-1Ra.

144. The method according to Clause 142, wherein the method results in the production of antibodies to a vector comprising a coding sequence for IL-1Ra.

145. The method according to any of the preceding clauses, wherein the human has pre-existing antibodies to a vector comprising a coding sequence for IL-1Ra.

146. The method according to any of the preceding clauses, wherein the human does not have pre-existing antibodies to a vector comprising a coding sequence for IL-1Ra at a titer greater than 1:5.

147. The method according to Clause 146, wherein the human does not have pre-existing antibodies to a vector comprising a coding sequence for IL-1Ra at a titer greater than 1:10.

148. The method according to Clause 147, wherein the human does not have pre-existing antibodies to a vector comprising a coding sequence for IL-1Ra at a titer greater than 1:20.

149. The method according to Clause 148, wherein the human does not have pre-existing antibodies to a vector comprising a coding sequence for IL-1Ra at a titer greater than 1:40.

150. The method according to Clause 149, wherein the human does not have pre-existing antibodies to a vector comprising a coding sequence for IL-1Ra at a titer greater than 1:80.

151. The method according to any of the preceding clauses, wherein the method further comprises administering a second osteoarthritis therapy to the human.

152. The method according to Clause 151, wherein the second osteoarthritis therapy is selected from the group consisting of: acetaminophen therapy, non-steroidal anti-inflammatory drug therapy, opiate therapy, glucocorticoid therapy, hyaluronic acid therapy, stem cell therapy, autologous blood product therapy, and combinations thereof.

153. The method according to Clause 152, wherein the autologous blood product therapy comprises platelet rich plasma therapy.

154. A human safe pharmaceutical unit dose comprising an AAV vector comprising a coding sequence for a human IL-1Ra at and an aqueous delivery vehicle.

155. The pharmaceutical unit dose according to Clause 154, wherein the coding sequence comprises a naturally occurring coding sequence.

156. The pharmaceutical unit dose according to Clause 155, wherein the coding sequence comprises a non-naturally occurring coding sequence.

157. The pharmaceutical unit dose according to Clause 156, wherein the coding sequence comprises a codon-optimized coding sequence.

158. The pharmaceutical unit dose according to Clause 157, wherein the coding sequence comprises a sequence that is 95% or more identical to SEQ ID NOs: 04 or 05.

159. The pharmaceutical unit dose according to any of Clauses 154 to 158, wherein the AAV vector is selected from the group consisting of AAV1, AAV2, AAV2.5, AAV3, AAV4, AAV5, AAV6, AAV7, AAV8, AAV9, AAV10, AAV11, AAV12 and Anc80.

160. The pharmaceutical unit dose according to Clause 159, wherein the AAV vector is an AAV2.5 vector.

161. The pharmaceutical unit dose according to Clause 160, wherein the vector has a cap protein having a sequence that is 95% or more identical to SEQ ID NOs: 08 or 10.

162. The pharmaceutical unit dose according to any of Clauses 154 to 161, wherein the AAV vector is a self-complementary AAV (scAAV) vector.

163. The pharmaceutical unit dose according to any of Clauses 154 to 162, wherein the coding sequence is operatively linked to a promoter.

164. The pharmaceutical unit dose according to Clause 163, wherein the promoter is a non-human promoter.

165. The pharmaceutical unit dose according to Clause 164, wherein the promoter is a viral promoter.

166. The pharmaceutical unit dose according to Clause 165, wherein the promoter is a cytomegalovirus immediate early promoter.

167. The pharmaceutical unit dose according to any of Clauses 154 to 165, wherein 90% or less of the viral particles in the dose are empty.

168. The pharmaceutical unit dose according to Clause 167, wherein 80% or less of the viral particles in the dose are empty.

169. The pharmaceutical unit dose according to Clause 168, wherein 70% or less of the viral particles in the dose are empty.

170. The pharmaceutical unit dose according to Clause 169, wherein 60% or less of the viral particles in the dose are empty.

171. The pharmaceutical unit dose according to Clause 170, wherein 50% or less of the viral particles in the dose are empty.

172. The pharmaceutical unit dose according to Clause 171, wherein 40% or less of the viral particles in the dose are empty.

173. The pharmaceutical unit dose according to Clause 172, wherein 30% or less of the viral particles in the dose are empty.

174. The pharmaceutical unit dose according to Clause 173, wherein 20% or less of the viral particles in the dose are empty.

175. The pharmaceutical unit dose according to Clause 174, wherein 10% or less of the viral particles in the dose are empty.

176. The pharmaceutical unit dose according to any of Clauses 154 to 166, wherein 10% or more of the viral particles in the dose are full.

177. The pharmaceutical unit dose according to Clause 176, wherein 20% or more of the viral particles in the dose are full.

178. The pharmaceutical unit dose according to Clause 177, wherein 30% or more of the viral particles in the dose are full.

179. The pharmaceutical unit dose according to Clause 178, wherein 40% or more of the viral particles in the dose are full.

180. The pharmaceutical unit dose according to Clause 179, wherein 50% or more of the viral particles in the dose are full.

181. The pharmaceutical unit dose according to Clause 180, wherein 60% or more of the viral particles in the dose are full.

182. The pharmaceutical unit dose according to Clause 181, wherein 70% or more of the viral particles in the dose are full.

183. The pharmaceutical unit dose according to Clause 182, wherein 80% or more of the viral particles in the dose are full.

184. The pharmaceutical unit dose according to Clause 183, wherein 90% or more of the viral particles in the dose are full.

185. The pharmaceutical unit dose according to any of Clauses 167 to 184, wherein the proportion of empty particles is determined by a method selected from analytical ultracentrifugation (AUC), transmission electron microscopy (TEM), the ratio of genomes (qPCR) to capsid particles (ELISA), or analytical HPLC.

186. The pharmaceutical unit dose according to any of Clauses 154 to 185, wherein the aqueous delivery vehicle comprises a buffer.

187. The pharmaceutical unit dose according to Clause 186, wherein the buffer comprises a phosphate buffer.

188. The pharmaceutical unit dose according to any of Clauses 154 to 187, wherein the aqueous delivery vehicle comprises a salt.

189. The pharmaceutical unit dose according to Clause 188, wherein the salt is NaCl.

190. The pharmaceutical unit dose according to any of Clauses 154 to 189, wherein the aqueous delivery vehicle comprises a polyol.

191. The pharmaceutical unit dose according to Clause 190, wherein the polyol comprises a sugar alcohol.

192. The pharmaceutical unit dose according to Clause 191, wherein the sugar alcohol is sorbitol.

193. The pharmaceutical unit dose of according to any of Clauses 154 to 192, wherein the aqueous delivery vehicle comprises a surfactant.

194. The pharmaceutical unit dose according to Clause 193, wherein the surfactant is a polymer.

195. The pharmaceutical unit dose according to Clause 194, wherein the polymer is block copolymer.

196. The pharmaceutical unit dose according to Clause 195, wherein the block copolymer is a polyalkylene glycol.

197. The pharmaceutical unit dose according to Clause 196, wherein the polyalkylene glycol is a poloxamer.

198. The pharmaceutical unit dose according to any of Clauses 154 to 197, wherein the dose comprises from $1\times10^8$ to $2\times10^{13}$ viral vector genomes.

199. The pharmaceutical unit dose according to Clause 198, wherein the dose comprises from $1\times10^8$ to $1\times10^{13}$ viral vector genomes.

200. The pharmaceutical unit dose according to Clause 199, wherein the dose comprises from $1\times10^{11}$ to $1\times10^{13}$ viral vector genomes.

201. The pharmaceutical unit dose according to Clause 198, wherein the dose comprises from $2\times10^{11}$ to $2\times10^{13}$ viral vector genomes.

202. The pharmaceutical unit dose according to any of Clauses 154 to 201, wherein the dose has a volume ranging from 0.25 to 25 ml.

203. The pharmaceutical unit dose according to Clause 202, wherein the dose has a volume ranging from 2 to 12 ml.

204. The pharmaceutical unit dose according to Clause 203, wherein the dose has a volume ranging from 2 to 5 ml.

205. The pharmaceutical unit dose according to Clause 203, wherein the dose has a volume ranging from 9 to 11 ml.

206. The pharmaceutical unit dose according to any of Clauses 154 to 205, wherein the dose has been stored at a temperature between −60 to −80° C. for 1 day or longer.

207. The pharmaceutical unit dose according to Clause 206, wherein the dose has been stored at a temperature between −60 to −80° C. for 1 week or longer.

208. The pharmaceutical unit dose according to Clause 207, wherein the dose has been stored at a temperature between −60 to −80° C. for 1 month or longer.

209. The pharmaceutical unit dose according to Clause 208, wherein the dose has been stored at a temperature between −60 to −80° C. for 6 months or longer.

210. The pharmaceutical unit dose according to Clause 209, wherein the dose has been stored at a temperature between −60 to −80° C. for 1 year or longer.

211. The pharmaceutical unit dose according to Clause 210, wherein the dose has been stored at a temperature between −60 to −80° C. for 2 years or longer.

212. The pharmaceutical unit dose according to Clause 211, wherein the dose has been stored at a temperature between −60 to −80° C. for 5 years or longer.

213. The pharmaceutical unit dose according to any of Clauses 154 to 205, wherein the dose has been stored at a temperature ranging from 2 to 8° C. for 1 day or longer.

214. The pharmaceutical unit dose according to Clause 213, wherein the dose has been stored at a temperature ranging from 2 to 8° C. for 2 days or longer.

215. The pharmaceutical unit dose according to Clause 214, wherein the dose has been stored at a temperature ranging from 2 to 8° C. for 3 days or longer.

216. The pharmaceutical unit dose according to Clause 214, wherein the dose has been stored at a temperature ranging from 2 to 8° C. for 4 days or longer.

217. The pharmaceutical unit dose according to Clause 216, wherein the dose has been stored at a temperature ranging from 2 to 8° C. for 5 days or longer.

218. The pharmaceutical unit dose according to Clause 217, wherein the dose has been stored at a temperature ranging from 2 to 8° C. for 6 days or longer.

219. The pharmaceutical unit dose according to Clause 218, wherein the dose has been stored at a temperature ranging from 2 to 8° C. for 7 days or longer.

220. The pharmaceutical unit dose according to Clause 219, wherein the dose has been stored at a temperature ranging from 2 to 8° C. for 8 days or longer.

221. The pharmaceutical unit dose according to Clause 220, wherein the dose has been stored at a temperature ranging from 2 to 8° C. for 9 days or longer.

222. The pharmaceutical unit dose according to Clause 221, wherein the dose has been stored at a temperature ranging from 2 to 8° C. for 10 days or longer.

223. The pharmaceutical unit dose according to Clause 222, wherein the dose has been stored at a temperature ranging from 2 to 8° C. for 11 days or longer.

224. The pharmaceutical unit dose according to Clause 223, wherein the dose has been stored at a temperature ranging from 2 to 8° C. for 12 days or longer.

225. The pharmaceutical unit dose according to Clause 224, wherein the dose has been stored at a temperature ranging from 2 to 8° C. for 13 days or longer.

226. The pharmaceutical unit dose according to Clause 225, wherein the dose has been stored at a temperature ranging from 2 to 8° C. for 14 days or longer.

227. A kit comprising:

a pre-unit dose comprising an AAV vector comprising a coding sequence for a human IL-1Ra; and a diluent;

wherein combination of the diluent with the pre-unit dose produces a safe pharmaceutical unit dose comprising an AAV vector comprising a coding sequence for a human IL-1Ra at and an aqueous delivery vehicle.

228. The kit according to Clause 227, wherein the coding sequence comprises a naturally occurring coding sequence.

229. The kit according to Clause 228, wherein the coding sequence comprises a non-naturally occurring coding sequence.

230. The kit according to Clause 229, wherein the coding sequence comprises a codon-optimized coding sequence.

231. The kit according to Clause 230, wherein the coding sequence comprises a sequence that is 95% or more identical to SEQ ID NOs:04 or 05.

232. The kit according to any of Clauses 227 to 231, wherein the AAV vector is selected from the group consisting of AAV1, AAV2, AAV2.5, AAV3, AAV4, AAV5, AAV6, AAV7, AAV8, AAV9, AAV10, AAV11, AAV12 and Anc80.

233. The kit according to Clause 232, wherein the AAV vector is an AAV2.5 vector.

234. The kit according to Clause 233, wherein the vector has a cap protein having a sequence that is 95% or more identical to SEQ ID NOs: 08 or 10.

235. The kit according to any of Clauses 227 to 234, wherein the AAV vector is a self-complementary AAV (scAAV) vector.

236. The kit according to any of Clauses 227 to 235, wherein the coding sequence is operatively linked to a promoter.

237. The kit according to Clause 236, wherein the promoter is a non-human promoter.

238. The kit according to Clause 237, wherein the promoter is a viral promoter.

239. The kit according to Clause 238, wherein the promoter is a cytomegalovirus immediate early promoter.

240. The kit according to any of Clauses 227 to 239, wherein 90% or less of the viral particles in the pharmaceutical unit dose are empty.

241. The kit according to Clause 240, wherein 80% or less of the viral particles in the pharmaceutical unit dose are empty.

242. The kit according to Clause 241, wherein 70% or less of the viral particles in the pharmaceutical unit dose are empty.

243. The kit according to Clause 242, wherein 60% or less of the viral particles in the pharmaceutical unit dose are empty.

244. The kit according to Clause 243, wherein 50% or less of the viral particles in the pharmaceutical unit dose are empty.

245. The kit according to Clause 244, wherein 40% or less of the viral particles in the pharmaceutical unit dose are empty.

246. The kit according to Clause 245, wherein 30% or less of the viral particles in the pharmaceutical unit dose are empty.

247. The kit according to Clause 246, wherein 20% or less of the viral particles in the pharmaceutical unit dose are empty.

248. The kit according to Clause 247, wherein 10% or less of the viral particles in the pharmaceutical unit does are empty.

249. The kit according to any of Clauses 227 to 239, wherein 10% or more of the viral particles in the pharmaceutical unit dose are full.

250. The kit according to Clause 249, wherein 20% or more of the viral particles in the pharmaceutical unit dose are full.

251. The kit according to Clause 250, wherein 30% or more of the viral particles in the pharmaceutical unit dose are full.

252. The kit according to Clause 251, wherein 40% or more of the viral particles in the pharmaceutical unit dose are full.

253. The kit according to Clause 252, wherein 50% or more of the viral particles in the pharmaceutical unit dose are full.

254. The kit according to Clause 253, wherein 60% or more of the viral particles in the pharmaceutical unit dose are full.

255. The kit according to Clause 254, wherein 70% or more of the viral particles in the pharmaceutical unit dose are full.

256. The kit according to Clause 255, wherein 80% or more of the viral particles in the pharmaceutical unit dose are full.

257. The kit according to Clause 256, wherein 90% or more of the viral particles in the pharmaceutical unit dose are full.

258. The kit according to any of Clauses 240 to 257, wherein the proportion of empty particles is determined by a method selected from analytical ultracentrifugation (AUC), transmission electron microscopy (TEM), the ratio of genomes (qPCR) to capsid particles (ELISA), or analytical HPLC.

259. The kit according to any of Clauses 227 to 258, wherein the aqueous delivery vehicle comprises a buffer.

260. The kit according to Clause 259, wherein the buffer comprises a phosphate buffer.

261. The kit according to any of Clauses 227 to 260, wherein the aqueous delivery vehicle comprises a salt.

262. The kit according to Clause 261, wherein the salt is NaCl.

263. The kit according to any of Clauses 227 to 262, wherein the aqueous delivery vehicle comprises a polyol.

264. The kit according to Clause 263, wherein the polyol comprises a sugar alcohol.

265. The kit according to Clause 264, wherein the sugar alcohol is sorbitol.

266. The kit according to any of Clauses 227 to 265, wherein the aqueous delivery vehicle comprises a surfactant.

267. The kit according to Clause 266, wherein the surfactant is a polymer.

268. The kit according to Clause 267, wherein the polymer is block copolymer.

269. The kit according to Clause 268, wherein the block copolymer is a polyalkylene glycol.

270. The kit according to Clause 269, wherein the polyalkylene glycol is a poloxamer.

271. The kit according to any of Clauses 227 to 270, wherein the pharmaceutical unit dose comprises from $1\times10^8$ to $2\times10^{13}$ viral vector genomes.

272. The kit according to Clause 271, wherein the pharmaceutical unit dose comprises from $1\times10^8$ to $1\times10^{13}$ viral vector genomes.

273. The kit according to Clause 272, wherein the pharmaceutical unit dose comprises from $1\times10^{11}$ to $1\times10^{13}$ viral vector genomes.

274. The kit according to Clause 271, wherein the pharmaceutical unit dose comprises from $2\times10^{11}$ to $2\times10^{13}$ viral vector genomes.

275. The kit according to any of Clauses 227 to 274, wherein the pharmaceutical unit dose has a volume ranging from 0.5 to 15 ml.

276. The kit according to Clause 275, wherein the pharmaceutical unit dose has a volume ranging from 2 to 12 ml.

277. The kit according to Clause 276, wherein the pharmaceutical unit dose has a volume ranging from 2 to 5 ml.

278. The kit according to Clause 276, wherein the pharmaceutical unit dose has a volume ranging from 9 to 11 ml.

279. The kit according to any of Clauses 227 to 278, wherein the kit further comprises a syringe.

280. The kit according any of Clauses 227 to 279, wherein the kit further comprises a needle.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method for treating osteoarthritis in a human suffering from osteoarthritis, the method comprising:

intra-articularly administering a dosage comprising a nucleic acid coding sequence for a human interleukin-1 receptor antagonist (IL-1Ra) to the human to treat osteoarthritis in the human suffering from osteoarthritis to provide a synovial fluid IL-1Ra concentration ranging from 0.1 ng/ml to 400 ng/ml for a period of 6 months or longer following administration to treat the human suffering from osteoarthritis.

2. The method according to claim 1, wherein the coding sequence comprises a sequence that is 95% or more identical to SEQ ID NOS: 04 or 05.

3. The method according to claim 1, wherein the coding sequence is present in a vector.

4. The method according to claim 3, wherein the vector is a viral vector.

5. The method according to claim 4, wherein the viral vector is non-integrating viral vector.

6. The method according to claim 5, wherein the non-integrating viral vector is an adeno-associated virus (AAV) vector.

7. The method according to claim 6, wherein the AAV vector is a self-complementary AAV (scAAV) vector.

8. The method according to claim 1, wherein the coding sequence is operatively linked to a promoter.

9. The method according to claim 6, wherein the dosage comprises from $1\times10^{8}$ to $2\times10^{13}$ viral vector genomes.

10. The method according to claim 1, wherein the dosage has a volume ranging from 0.25 to 25 ml.

11. The method according to claim 1, wherein the human is an adult.

12. The method according to claim 1, wherein the osteoarthritis is selected from the group consisting osteoarthritis of the hand, knee, hip, shoulder, ankle, elbow, temporomandibular joint, spine, and combinations thereof.

13. The method according to claim 12, wherein the osteoarthritis is osteoarthritis of the knee.

14. A human safe pharmaceutical unit dose comprising an AAV vector comprising a coding sequence for a human IL-1Ra at and an aqueous delivery vehicle.

15. The method according to claim 1, wherein the human has failed a three-month trial of a minimum of two conservative therapies for the osteoarthritis, wherein the conservative therapy is selected from the group consisting of activity modification, weight loss, physical therapy, steroid therapy, non-steroidal anti-inflammatory therapy and injection therapy.

16. The method according to claim 1, wherein the method results in a reduction in pain.

17. The method according to claim 16, wherein the magnitude of pain reduction is manifested by a movement along of a scale of 10% or more of the length of scale, wherein the scale is Visual Analog Scale (VAS), Western Ontario and McMaster Universities Arthritis Index (WOMAC) or Knee injury and Osteoarthritis Outcome Score (KOOS).

18. The method according to claim 1, wherein the method further comprises administering a second osteoarthritis therapy to the human.

19. The method according to claim 18, wherein the second osteoarthritis therapy is selected from the group consisting of acetaminophen therapy, non-steroidal anti-inflammatory drug therapy, opiate therapy, glucocorticoid therapy, hyaluronic acid therapy, stem cell therapy, autologous blood product therapy, and combinations thereof.

20. The method according to claim 1, wherein the period is a period of 12 months or longer.

* * * * *

UNITED STATES PATENT AND TRADEMARK OFFICE

CERTIFICATE OF CORRECTION

PATENT NO. : 12,370,240 B2
APPLICATION NO. : 17/295588
DATED : July 29, 2025
INVENTOR(S) : Thomas W. Chalberg, Jr. et al.

It is certified that error appears in the above-identified patent and that said Letters Patent is hereby corrected as shown below:

In the Specification

Please replace “In” with -- in -- (Column 1, Line 28).

Please replace “IDLSENRKQD” with -- TDLSENRKQD -- (Column 7, Line 8).

Please replace “r5419598” with -- rs419598 -- (Column 10, Line 54).

Please replace “r5315952,” with -- rs315952, -- (Column 10, Line 55).

Please replace “r5419598” with -- rs419598 -- (Column 10, Line 55).

Please replace “hemagglutinatin” with -- hemagglutinating -- (Column 11, Line 15).

Please replace “palendromic” with -- palindromic -- (Column 11, Lines 28-29).

Please replace “cholestrum-” with -- colostrum- -- (Column 18, Line 15).

Please replace “manitol,” with -- mannitol, -- (Column 20, Line 38).

Please replace “thereof” with -- thereof. -- (Column 20, Line 54).

Please replace “edemas)” with -- edema) -- (Column 23, Line 36).

Please replace “r5419598,” with -- rs419598, -- (Column 25, Line 67).

Please replace “r5315952,” with -- rs315952, -- (Column 26, Line 1).

Signed and Sealed this
Eighteenth Day of November, 2025

John A. Squires
*Director of the United States Patent and Trademark Office*

Please replace “a least” with -- at least -- (Column 29, Line 21).

Please replace “Sc-rAAV2.51L-1Ra” with -- Sc-rAAV2.5IL-1Ra -- (Column 31, Line 23).

Please replace “Sc-rAAV2.51L-1Ra” with -- Sc-rAAV2.5IL-1Ra -- (Column 31, Line 27).

Please replace “Sc-rAAV2.51L-1Ra.” with -- Sc-rAAV2.5IL-1Ra. -- (Column 31, Lines 40-41).

Please replace “Sc-rAAV2.51L-1Ra” with -- Sc-rAAV2.5IL-1Ra -- (Column 32, Line 61).

Please replace “188)).” with -- 188). -- (Column 36, Line 36).

Please replace “188)).” with -- 188). -- (Column 36, Line 43).

Please replace “Sc-rAAV2.51L-1Ra” with -- Sc-rAAV2.5IL-1Ra -- (Column 36, Line 48).

Please replace “Knee” with -- Knee. -- (Column 36, Line 49).

Please replace “Sc-rAAV2.51L-1Ra” with -- Sc-rAAV2.5IL-1Ra -- (Column 36, Line 54).

Please replace “r5419598/r5315952/rs9005.” with -- rs419598/rs315952/rs9005. -- (Column 37, Line 1).

Please replace “r5419598, r5315952,” with -- rs419598, rs315952, -- (Column 44, Line 62).

Please replace “r5419598 TT,” with -- rs419598 TT, -- (Column 44, Line 66).

Please replace “IL-1Ra at” with -- IL-1Ra -- (Column 47, Line 20).

Please replace “IL-1Ra at” with -- IL-1Ra -- (Column 50, Line 38).

Please replace “according” with -- according to -- (Column 52, Line 44).

In the Claims

Please replace “IL-1Ra at” with -- IL-1Ra -- (Column 72, Line 60).

SEQUENCE LISTING

```
<160> NUMBER OF SEQ ID NOS: 10

<210> SEQ ID NO 1
<211> LENGTH: 177
<212> TYPE: PRT
<213> ORGANISM: Homo sapiens

<400> SEQUENCE: 1

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu


<210> SEQ ID NO 2
<211> LENGTH: 153
<212> TYPE: PRT
<213> ORGANISM: Artificial sequence
<220> FEATURE:
<223> OTHER INFORMATION: synthetic sequence

<400> SEQUENCE: 2

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60
```

```
Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150
```

<210> SEQ ID NO 3
<211> LENGTH: 531
<212> TYPE: DNA
<213> ORGANISM: Homo sapiens

<400> SEQUENCE: 3

```
atggaaatct gcagaggcct ccgcagtcac ctaatcactc tcctcctctt cctgttccat     60

tcagagacga tctgccgacc ctctgggaga aaatccagca agatgcaagc cttcagaatc    120

tgggatgtta accagaagac cttctatctg aggaacaacc aactagttgc tggatacttg    180

caaggaccaa atgtcaattt agaagaaaag atagatgtgg tacccattga gcctcatgct    240

ctgttcttgg gaatccatgg agggaagatg tgcctgtcct gtgtcaagtc tggtgatgag    300

accagactcc agctggaggc agttaacatc actgacctga gcgagaacag aaagcaggac    360

aagcgcttcg ccttcatccg ctcagacagt ggccccacca ccagttttga gtctgccgcc    420

tgccccggtt ggttcctctg cacagcgatg gaagctgacc agcccgtcag cctcaccaat    480

atgcctgacg aaggcgtcat ggtcaccaaa ttctacttcc aggaggacga g             531
```

<210> SEQ ID NO 4
<211> LENGTH: 534
<212> TYPE: DNA
<213> ORGANISM: Artificial sequence
<220> FEATURE:
<223> OTHER INFORMATION: synthetic sequence

<400> SEQUENCE: 4

```
atggaaatct gcagaggcct gcggagccac ctgattaccc tgctgctgtt cctgttccac     60

agcgagacaa tctgccggcc cagcggccgg aagtccagca agatgcaggc cttccggatc    120

tgggacgtga accagaaaac cttctacctg cggaacaacc agctggtggc cggatacctg    180

cagggcccca acgtgaacct ggaagagaag atcgacgtgg tgcccatcga gccccacgcc    240

ctgtttctgg gcatccacgg cggcaagatg tgcctgagct gcgtgaagtc cggcgacgag    300

acaagactgc agctggaagc cgtgaacatc accgacctga gcgagaaccg gaagcaggac    360

aagagattcg ccttcatcag aagcgacagc ggccccacca ccagctttga gagcgccgcc    420

tgccccggct ggttcctgtg tacagccatg gaagccgacc agcccgtgtc cctgacaaac    480

atgcccgacg agggcgtgat ggtcaccaag ttctattttc aagaagatga gtaa          534
```

<210> SEQ ID NO 5
<211> LENGTH: 531
<212> TYPE: DNA
<213> ORGANISM: Artificial sequence
<220> FEATURE:
<223> OTHER INFORMATION: synthetic sequence

```
<400> SEQUENCE: 5

atggaaattt gccgcggcct gcgcagccat ctgattaccc tgctgctgtt tctgtttcat     60

agcgaaacca tttgccgccc gagcggccgc aaaagcagca aaatgcaggc gtttcgcatt    120

tgggatgtga accagaaaac cttttatctg cgcaacaacc agctggtggc gggctatctg    180

cagggcccga acgtgaacct ggaagaaaaa attgatgtgg tgccgattga accgcatgcg    240

ctgtttctgg gcattcatgg cggcaaaatg tgcctgagct gcgtgaaaag cggcgatgaa    300

acccgcctgc agctggaagc ggtgaacatt accgatctga gcgaaaaccg caaacaggat    360

aaacgctttg cgtttattcg cagcgatagc ggcccgacca ccagctttga aagcgcggcg    420

tgcccgggct ggtttctgtg caccgcgatg gaagcggatc agccggtgag cctgaccaac    480

atgccggatg aaggcgtgat ggtgaccaaa ttttattttc aggaagatga a             531


<210> SEQ ID NO 6
<211> LENGTH: 531
<212> TYPE: PRT
<213> ORGANISM: Artificial sequence
<220> FEATURE:
<223> OTHER INFORMATION: synthetic sequence

<400> SEQUENCE: 6

Ala Thr Gly Gly Ala Arg Ala Thr His Thr Gly Tyr Met Gly Asn Gly
1               5                   10                  15

Gly Asn Tyr Thr Asn Met Gly Asn Trp Ser Asn Cys Ala Tyr Tyr Thr
            20                  25                  30

Asn Ala Thr His Ala Cys Asn Tyr Thr Asn Tyr Thr Asn Tyr Thr Asn
        35                  40                  45

Thr Thr Tyr Tyr Thr Asn Thr Thr Tyr Cys Ala Tyr Trp Ser Asn Gly
    50                  55                  60

Ala Arg Ala Cys Asn Ala Thr His Thr Gly Tyr Met Gly Asn Cys Cys
65                  70                  75                  80

Asn Trp Ser Asn Gly Gly Asn Met Gly Asn Ala Ala Arg Trp Ser Asn
                85                  90                  95

Trp Ser Asn Ala Ala Arg Ala Thr Gly Cys Ala Arg Gly Cys Asn Thr
            100                 105                 110

Thr Tyr Met Gly Asn Ala Thr His Thr Gly Gly Gly Ala Tyr Gly Thr
        115                 120                 125

Asn Ala Ala Tyr Cys Ala Arg Ala Ala Arg Ala Cys Asn Thr Thr Tyr
    130                 135                 140

Thr Ala Tyr Tyr Thr Asn Met Gly Asn Ala Ala Tyr Ala Ala Tyr Cys
145                 150                 155                 160

Ala Arg Tyr Thr Asn Gly Thr Asn Gly Cys Asn Gly Gly Asn Thr Ala
                165                 170                 175

Tyr Tyr Thr Asn Cys Ala Arg Gly Gly Asn Cys Cys Asn Ala Ala Tyr
            180                 185                 190

Gly Thr Asn Ala Ala Tyr Tyr Thr Asn Gly Ala Arg Gly Ala Arg Ala
        195                 200                 205

Ala Arg Ala Thr His Gly Ala Tyr Gly Thr Asn Gly Thr Asn Cys Cys
    210                 215                 220

Asn Ala Thr His Gly Ala Arg Cys Cys Asn Cys Ala Tyr Gly Cys Asn
225                 230                 235                 240

Tyr Thr Asn Thr Thr Tyr Tyr Thr Asn Gly Gly Asn Ala Thr His Cys
                245                 250                 255
```

```
Ala Tyr Gly Gly Asn Gly Gly Asn Ala Ala Arg Ala Thr Gly Thr Gly
            260                 265                 270

Tyr Tyr Thr Asn Trp Ser Asn Thr Gly Tyr Gly Thr Asn Ala Ala Arg
        275                 280                 285

Trp Ser Asn Gly Gly Asn Gly Ala Tyr Gly Ala Arg Ala Cys Asn Met
    290                 295                 300

Gly Asn Tyr Thr Asn Cys Ala Arg Tyr Thr Asn Gly Ala Arg Gly Cys
305                 310                 315                 320

Asn Gly Thr Asn Ala Ala Tyr Ala Thr His Ala Cys Asn Gly Ala Tyr
                325                 330                 335

Tyr Thr Asn Trp Ser Asn Gly Ala Arg Ala Ala Tyr Met Gly Asn Ala
            340                 345                 350

Ala Arg Cys Ala Arg Gly Ala Tyr Ala Ala Arg Met Gly Asn Thr Thr
        355                 360                 365

Tyr Gly Cys Asn Thr Thr Tyr Ala Thr His Met Gly Asn Trp Ser Asn
    370                 375                 380

Gly Ala Tyr Trp Ser Asn Gly Gly Asn Cys Cys Asn Ala Cys Asn Ala
385                 390                 395                 400

Cys Asn Trp Ser Asn Thr Thr Tyr Gly Ala Arg Trp Ser Asn Gly Cys
                405                 410                 415

Asn Gly Cys Asn Thr Gly Tyr Cys Cys Asn Gly Gly Asn Thr Gly Gly
            420                 425                 430

Thr Thr Tyr Tyr Thr Asn Thr Gly Tyr Ala Cys Asn Gly Cys Asn Ala
        435                 440                 445

Thr Gly Gly Ala Arg Gly Cys Asn Gly Ala Tyr Cys Ala Arg Cys Cys
    450                 455                 460

Asn Gly Thr Asn Trp Ser Asn Tyr Thr Asn Ala Cys Asn Ala Ala Tyr
465                 470                 475                 480

Ala Thr Gly Cys Cys Asn Gly Ala Tyr Gly Ala Arg Gly Gly Asn Gly
                485                 490                 495

Thr Asn Ala Thr Gly Gly Thr Asn Ala Cys Asn Ala Ala Arg Thr Thr
            500                 505                 510

Tyr Thr Ala Tyr Thr Thr Tyr Cys Ala Arg Gly Ala Arg Gly Ala Tyr
        515                 520                 525

Gly Ala Arg
    530
```

<210> SEQ ID NO 7
<211> LENGTH: 2208
<212> TYPE: DNA
<213> ORGANISM: Artificial sequence
<220> FEATURE:
<223> OTHER INFORMATION: synthetic sequence

<400> SEQUENCE: 7

```
atggctgccg atggttatct tccagattgg ctcgaggaca ctctctctga aggaataaga      60

cagtggtgga agctcaaacc tggcccacca ccaccaaagc ccgcagagcg gcataaggac     120

gacagcaggg gtcttgtgct tcctgggtac aagtacctcg gacccttcaa cggactcgac     180

aagggagagc cggtcaacga ggcagacgcc gcggccctcg agcacgacaa agcctacgac     240

cggcagctcg acagcggaga caacccgtac ctcaagtaca accacgccga cgcggagttt     300

caggagcgcc ttaaagaaga tacgtctttt gggggcaacc tcggacgagc agtcttccag     360

gcgaaaaaga gggttcttga acctctgggc ctggttgagg aacctgttaa gacggctccg     420

ggaaaaaaga ggccggtaga gcactctcct gtggagccag actcctcctc gggaaccgga     480
```

```
aaggcgggcc agcagcctgc aagaaaaaga ttgaattttg gtcagactgg agacgcagac    540

tcagtacctg acccccagcc tctcggacag ccaccagcag ccccctctgg tctgggaact    600

aatacgatgg ctacaggcag tggcgcacca atggcagaca ataacgaggg cgccgacgga    660

gtgggtaatt cctcgggaaa ttggcattgc gattccacat ggatgggcga cagagtcatc    720

accaccagca cccgaacctg ggccctgccc acctacaaca accacctcta caaacaaatt    780

tccagccaat caggagcctc gaacgacaat cactactttg gctacagcac cccttggggg    840

tattttgact tcaacagatt ccactgccac ttttcaccac gtgactggca aagactcatc    900

aacaacaact ggggattccg acccaagaga ctcaacttca agctctttaa cattcaagtc    960

aaagaggtca cgcagaatga cggtacgacg acgattgcca ataaccttac cagcacggtt   1020

caggtgttta ctgactcgga gtaccagctc ccgtacgtcc tcggctcggc gcatcaagga   1080

tgcctcccgc cgttcccagc agacgtcttc atggtgccac agtatggata cctcaccctg   1140

aacaacggga gtcaggcagt aggacgctct tcattttact gcctggagta ctttccttct   1200

cagatgctgc gtaccggaaa caactttacc ttcagctaca cttttgagga cgttcctttc   1260

cacagcagct acgctcacag ccagagtctg gaccgtctca tgaatcctct catcgaccag   1320

tacctgtatt acttgagcag aacaaacact ccaagtggaa ccaccacgca gtcaaggctt   1380

cagttttctc aggccggagc gagtgacatt cgggaccagt ctaggaactg gcttcctgga   1440

ccctgttacc gccagcagcg agtatcaaag acatctgcgg ataacaacaa cagtgaatac   1500

tcgtggactg gagctaccaa gtaccacctc aatggcagag actctctggt gaatccgggc   1560

ccggccatgg caagccacaa ggacgatgaa gaaaagtttt ttcctcagag cggggttctc   1620

atctttggga agcaaggctc agagaaaaca aatgtggaca ttgaaaaggt catgattaca   1680

gacgaagagg aaatcaggac aaccaatccc gtggctacgg agcagtatgg ttctgtatct   1740

accaacctcc agagaggcaa cagacaagca gctaccgcag atgtcaacac acaaggcgtt   1800

cttccaggca tggtctggca ggacagagat gtgtaccttc aggggcccat ctgggcaaag   1860

attccacaca cggacggaca ttttcacccc tctcccctca tgggtggatt cggacttaaa   1920

caccctcctc cacagattct catcaagaac accccggtac ctgcgaatcc ttcgaccacc   1980

ttcagtgcgg caaagtttgc ttccttcatc acacagtact ccacgggaca ggtcagcgtg   2040

gagatcgagt gggagctgca gaaggaaaac agcaaacgct ggaatcccga aattcagtac   2100

acttccaact acaacaagtc tgttaatgtg gactttactg tggacactaa tggcgtgtat   2160

tcagagcctc gccccattgg caccagatac ctgactcgta atctgtaa                2208
```

<210> SEQ ID NO 8
<211> LENGTH: 735
<212> TYPE: PRT
<213> ORGANISM: Artificial sequence
<220> FEATURE:
<223> OTHER INFORMATION: synthetic sequence

<400> SEQUENCE: 8

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45
```

```
Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460
```

```
Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 9
<211> LENGTH: 2211
<212> TYPE: DNA
<213> ORGANISM: Artificial sequence
<220> FEATURE:
<223> OTHER INFORMATION: synthetic sequence

<400> SEQUENCE: 9

```
atggctgccg atggttatct tccagattgg ctcgaggaca ctctctctga aggaataaga      60

cagtggtgga agctcaaacc tggcccacca ccaccaaagc ccgcagagcg gcataaggac     120

gacagcaggg gtcttgtgct tcctgggtac aagtacctcg gacccttcaa cggactcgac     180

aagggagagc cggtcaacga ggcagacgcc gcggccctcg agcacgacaa agcctacgac     240

cggcagctcg acagcggaga caacccgtac ctcaagtaca accacgccga cgcggagttt     300

caggagcgcc ttaaagaaga tacgtctttt gggggcaacc tcggacgagc agtcttccag     360

gcgaaaaaga gggttcttga acctctgggc ctggttgagg aacctgttaa gacggctccg     420

ggaaaaaaga ggccggtaga gcactctcct gtggagccag actcctcctc gggaaccgga     480

aaggcgggcc agcagcctgc aagaaaaaga ttgaattttg gtcagactgg agacgcagac     540
```

```
tcagtacctg acccccagcc tctcggacag ccaccagcag ccccctctgg tctgggaact    600

aatacgatgg ctacaggcag tggcgcacca atggcagaca ataacgaggg cgccgacgga    660

gtgggtaatt cctcgggaaa ttggcattgc gattccacat ggatgggcga cagagtcatc    720

accaccagca cccgaacctg ggccctgccc acctacaaca accacctcta caaacaaatt    780

tccagcgctt caacgggagc ctcgaacgac aatcactact ttggctacag caccccttgg    840

gggtattttg acttcaacag attccactgc cacttttcac cacgtgactg gcaaagactc    900

atcaacaaca actggggatt ccgacccaag agactcaact tcaagctctt taacattcaa    960

gtcaaagagg tcacgcagaa tgacggtacg acgacgattg ccaataacct taccagcacg   1020

gttcaggtgt ttactgactc ggagtaccag ctcccgtacg tcctcggctc ggcgcatcaa   1080

ggatgcctcc cgccgttccc agcagacgtc ttcatggtgc cacagtatgg atacctcacc   1140

ctgaacaacg ggagtcaggc agtaggacgc tcttcatttt actgcctgga gtactttcct   1200

tctcagatgc tgcgtaccgg aaacaacttt accttcagct acacttttga ggacgttcct   1260

ttccacagca gctacgctca cagccagagt ctggaccgtc tcatgaatcc tctcatcgac   1320

cagtacctgt attacttgag cagaacaaac actccaagtg gaaccaccac gcagtcaagg   1380

cttcagtttt ctcaggccgg agcgagtgac attcgggacc agtctaggaa ctggcttcct   1440

ggaccctgtt accgccagca gcgagtatca aagacatctg cggataacaa caacagtgaa   1500

tactcgtgga ctggagctac caagtaccac ctcaatggca gagactctct ggtgaatccg   1560

ggcccggcca tggcaagcca caaggacgat gaagaaaagt tttttcctca gagcggggtt   1620

ctcatctttg ggaagcaagg ctcagagaaa acaaatgtgg acattgaaaa ggtcatgatt   1680

acagacgaag aggaaatcag gacaaccaat cccgtggcta cggagcagta tggttctgta   1740

tctaccaacc tccagagagg caacagacaa gcagctaccg cagatgtcaa cacacaaggc   1800

gttcttccag gcatggtctg gcaggacaga gatgtgtacc ttcaggggcc catctgggca   1860

aagattccac acacggacgg acattttcac ccctctcccc tcatgggtgg attcggactt   1920

aaacaccctc ctccacagat tctcatcaag aacacccccg tacctgcgaa tccttcgacc   1980

accttcagtg cggcaaagtt tgcttccttc atcacacagt actccacggg acaggtcagc   2040

gtggagatcg agtgggagct gcagaaggaa aacagcaaac gctggaatcc cgaaattcag   2100

tacacttcca actacgccaa gtctgccaat gtggacttta ctgtggacaa taatggcgtg   2160

tattcagagc ctcgccccat tggcaccaga tacctgactc gtaatctgta a            2211
```

<210> SEQ ID NO 10
<211> LENGTH: 736
<212> TYPE: PRT
<213> ORGANISM: Artificial sequence
<220> FEATURE:
<223> OTHER INFORMATION: synthetic sequence

<400> SEQUENCE: 10

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Gln Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Val Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Asn Thr Pro Ser Gly Thr Thr Thr Gln Ser Arg Leu Gln Phe Ser
    450                 455                 460

Gln Ala Gly Ala Ser Asp Ile Arg Asp Gln Ser Arg Asn Trp Leu Pro
465                 470                 475                 480
```

-continued

```
Gly Pro Cys Tyr Arg Gln Gln Arg Val Ser Lys Thr Ser Ala Asp Asn
                485                 490                 495

Asn Asn Ser Glu Tyr Ser Trp Thr Gly Ala Thr Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Gln Ser Gly Val Leu Ile Phe Gly
    530                 535                 540

Lys Gln Gly Ser Glu Lys Thr Asn Val Asp Ile Glu Lys Val Met Ile
545                 550                 555                 560

Thr Asp Glu Glu Glu Ile Arg Thr Thr Asn Pro Val Ala Thr Glu Gln
                565                 570                 575

Tyr Gly Ser Val Ser Thr Asn Leu Gln Arg Gly Asn Arg Gln Ala Ala
            580                 585                 590

Thr Ala Asp Val Asn Thr Gln Gly Val Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Ser Thr Thr Phe Ser Ala Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Ala Lys Ser Ala Asn Val Asp Phe Thr Val Asp Asn Asn Gly Val
705                 710                 715                 720

Tyr Ser Glu Pro Arg Pro Ile Gly Thr Arg Tyr Leu Thr Arg Asn Leu
                725                 730                 735
```